(12) United States Patent
Zhang et al.

(10) Patent No.: US 10,160,950 B2
(45) Date of Patent: Dec. 25, 2018

(54) METHODS OF MAINTAINING, EXPANDING AND DIFFERENTIATING NEURONAL SUBTYPE SPECIFIC PROGENITORS

(71) Applicant: Wisconsin Alumni Research Foundation, Madison, WI (US)

(72) Inventors: Su-Chun Zhang, Waunakee, WI (US); Zhongwei Du, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/016,934

(22) Filed: Feb. 5, 2016

(65) Prior Publication Data
US 2016/0152950 A1    Jun. 2, 2016

Related U.S. Application Data

(63) Continuation-in-part of application No. 14/194,130, filed on Feb. 28, 2014.

(60) Provisional application No. 62/112,441, filed on Feb. 5, 2015, provisional application No. 61/771,572, filed on Mar. 1, 2013.

(51) Int. Cl.
*C12N 5/00* (2006.01)
*C12N 5/0793* (2010.01)

(52) U.S. Cl.
CPC ........ *C12N 5/0619* (2013.01); *C12N 2501/15* (2013.01); *C12N 2501/155* (2013.01); *C12N 2501/16* (2013.01); *C12N 2501/41* (2013.01); *C12N 2501/415* (2013.01); *C12N 2501/42* (2013.01); *C12N 2501/727* (2013.01); *C12N 2506/02* (2013.01); *C12N 2506/45* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 7,972,850 B2 | 7/2011 | Zhang et al. | |
| 2004/0224887 A1* | 11/2004 | Jessel | C12N 5/0619 435/377 |
| 2008/0227137 A1* | 9/2008 | Zhang | C12N 5/0623 435/29 |
| 2011/0091927 A1* | 4/2011 | Reubinoff | C12N 5/0619 435/29 |
| 2015/0010515 A1* | 1/2015 | Schoeler | A61K 35/30 424/93.7 |

FOREIGN PATENT DOCUMENTS

WO    WO 2013104752    * 7/2013

OTHER PUBLICATIONS

Hao et al., ACS Chem Biol.; 5(2): 245-253, Feb. 19, 2010.*
Li et al., PNAS, 108(20):8299-8304, Epublished Apr. 27, 2011.*
Li et al., PNAS, 108(20):8299-8304, Epub Apr. 27, 2011.*
Amoroso, M.W. et al. "Accelerated high-yield generation of limb-innervating motor neurons from human stem cells." J Neurosci 33, 574-586 (2013).
Briscoe et al. "The specification of neuronal identity by graded sonic hedgehog signaling" Semin. Cell Dev. Biol. 10 (3)353-62 (1999).
Briscoe et al. "Regulatory pathways linking progenitor patterning, cell fates and neurogenesis in the ventral neural tube" Philos. Trans. R. Soc. Lond. B. Biol. Sci. 363(1489):57-70 (2008).
Boergermann et al. "Dorsomorphin and LDN-193189 inhibit BMP-mediated Smad, p38 and Akt signaling in C2C12" Int. J. Biochem. Cell Biol. 42(11):1802-7 (2010).
Chambers, S.M. et al. "Highly efficient neural conversion of human EE and iPS cells by dual inhibition of SMAD signaling." Nat Biotechnol vol. 27, 275-280 (2009).
Chen, H. et al. "Modeling ALS with iPSCs reveals that mutant SOD1 mis-regulates neurofilament balance in motor neurons" Cell Stem Cell vol. 14, 796-809, (2014).
Gonzalez, et al. "An iCRISPR platform for rapid, multiplexable, and inducible genome editing in human pluripotent stem cells." Cell Stem Cell col. 15, 215-226 (2014).
Hester, M.E. et al. "Rapid and efficient generation of functional motor neurons from human pluripotent stem cells using gene delivered transcription factor codes." Mol Ther vol. 19, 1905-1912, (2011).
Krenick et. al, "Specification of transplantable astroglial subtypes from human pluripotent stem cells" Nature Biotechnology 29(6): 528-534 (2011).
Krenick et al. "Directed differentiation of functional astroglial subtypes from human pluripotent stem cells" Nat. Protoc. 6(11): 1710-1717 (2011).
Lee, S.K. & Pfaff, S.L. Transcriptional networks regulating neuronal identity in the developing spinal cord. Nat Neurosci vol. 4 Suppl, 1183-1191, 2001.
Lewis, J., Notch signalling and the control of cell fate choices in vertebrates. Semin Cell Dev Biol vol. 9, 583-589, 1998.
Li, W. et al. "Rapid induction and long-term self-renewal of primitive neural precursors from human embryonic stem cells by small molecule inhibitors." Proc Natl Acad SCI U S A 108, 8299-8304, (2011).
Li, X.J. et al. "Specification of motoneurons from human embryonic stem cells." Nat Biotechnol 23, 215-221, (2005).

(Continued)

*Primary Examiner* — Kimberly Ballard
*Assistant Examiner* — Stacey N MacFarlane
(74) *Attorney, Agent, or Firm* — Quarles & Brady LLP

(57) ABSTRACT

Methods for expanding proliferating populations of neuronal subtype-specific progenitors and creating substantially pure populations of motor neurons are provided herein. In particular, the present invention provides methods for maintaining the unique gene profile and differentiation potential of neuronal subtype-specific progenitors, such as motor neuron progenitors and hindbrain serotonergic neural progenitors.

6 Claims, 12 Drawing Sheets
(11 of 12 Drawing Sheet(s) Filed in Color)
Specification includes a Sequence Listing.

(56) References Cited

OTHER PUBLICATIONS

Li, X.J. et al. "Directed differentiation of ventral spinal progenitors and motor neurons from human embryonic stem cells by small molecules." Stem Cells 26, 886-893, (2008).

Liu, H. et al. "Specification of neuronal and glial subtypes from human pluripotent stem cells." Cell Mol Life Sci 68, 3995-4008, (2011).

Lu, J. et al. "Generation of integration-free and region-specific neural progenitors from primate fibroblasts." Cell Rep 3, 1580-1591, (2013).

Meijer et al. "GSK-3-selective inhibitors derived from tyrian purple indirubins" Chem. Biol. 10(12):1255-66 (2003).

Neely, M.D. et al. "DMH1, a highly selective small molecule BMP inhibitor promotes neurogenesis of hiPSCs: comparison of PAX6 and SOX1 expression during neural induction." ACS Chem Neurosci 3, 482-491, (2012).

Novitch et al. "A requirement for retinoic acid-mediated transcriptional activation in ventral neural patterning and motor neuron specification", Neuron 40(1):81-95 (2003).

Qu, Q. et al. "High-efficiency motor neuron differentiation from human pluripotent stem cells and the function of Islet-1." Nat Commun 5, 3449, (2014).

Reinhardt, P. et al. "Derivation and expansion using only small molecules of human neural progenitors for neurodegenerative disease modeling." PLoS One vol. 8, e59252, (2013).

Shirasaki "Transcriptional codes and the control of neuronal identity", Annu. Rev. Neurosci. 25:251-281 (2002).

Sinha et al. "Purmorphamine activates the hedgehog pathway by targeting smoothened", Nature Chem. Biol. 2:29-30 (2006).

Stockhausen, M.T., et al. "Effects of the histone deacetylase inhibitor valproic acid on Notch signalling in human neuroblastoma cells." Br J Cancer 92, 751-759, (2005).

Struder et al. "Transplantation of expanded mesencephalic precursors leads to recovery in parkinsonian rats", Nat. Neurosci. 1:290-295 (1998).

Temple "The development of neural stem cells" Nature 414:112-117 (2001).

Wang, H., et al. Tcf/Lef repressors differentially regulate Shh-Gli target gene activation thresholds to generate progenitor patterning in the developing CNS. Development 138, 3711-3721, (2011).

Weiss et al. "Is there a neural stem cell in the mammalian forebrain?" Trends Neurosci. 19:387-393 (1996).

Wichterle, H., et al. "Directed differentiation of embryonic stem cells into motor neurons." Cell 110, 385-397 (2002).

Wray, et al. "WNTing embryonic stem cells" Trends in Cell Biology 22:159-168 (2012).

Xi, J. et al. "Specification of midbrain dopamine neurons from primate pluripotent stem cells." Stem Cells 30, 1655-1663, (2012).

Zhang et al. "Embryonic stem cells for neural replacement therapy: prospects and challenges" J. Hematother. Stem Cell Res. 12:625-634 (2003).

\* cited by examiner

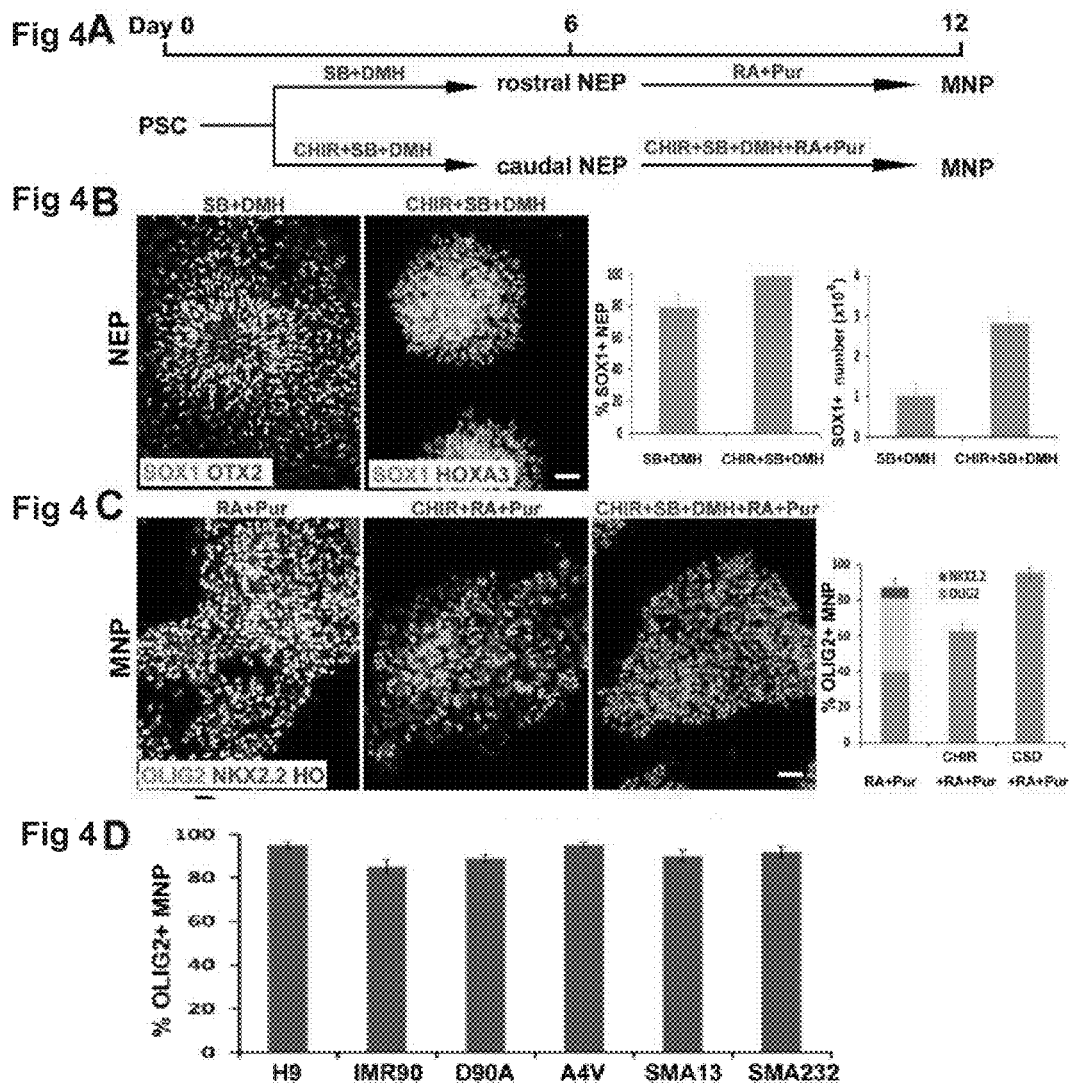
Figure 4A-D

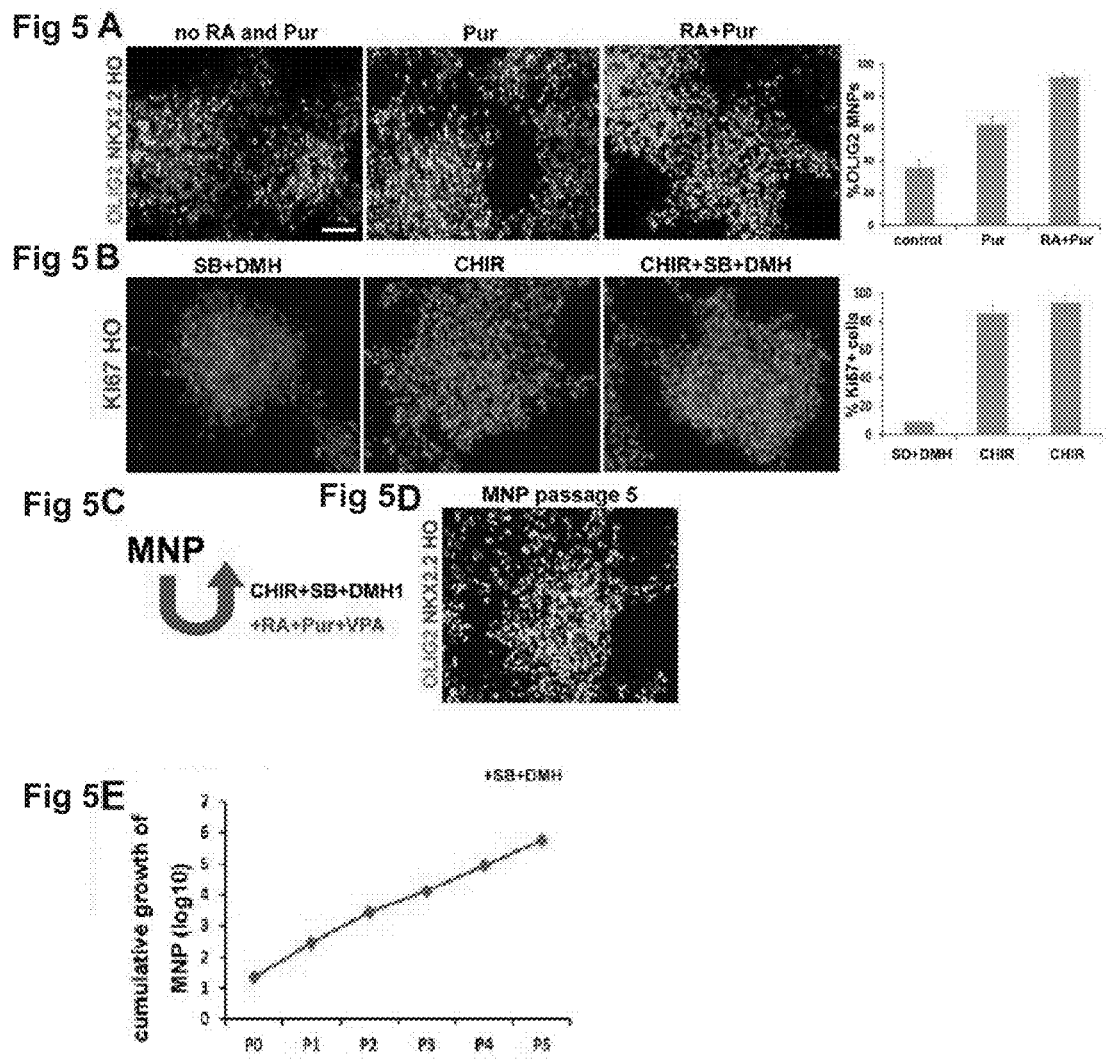
Figure 5A-E

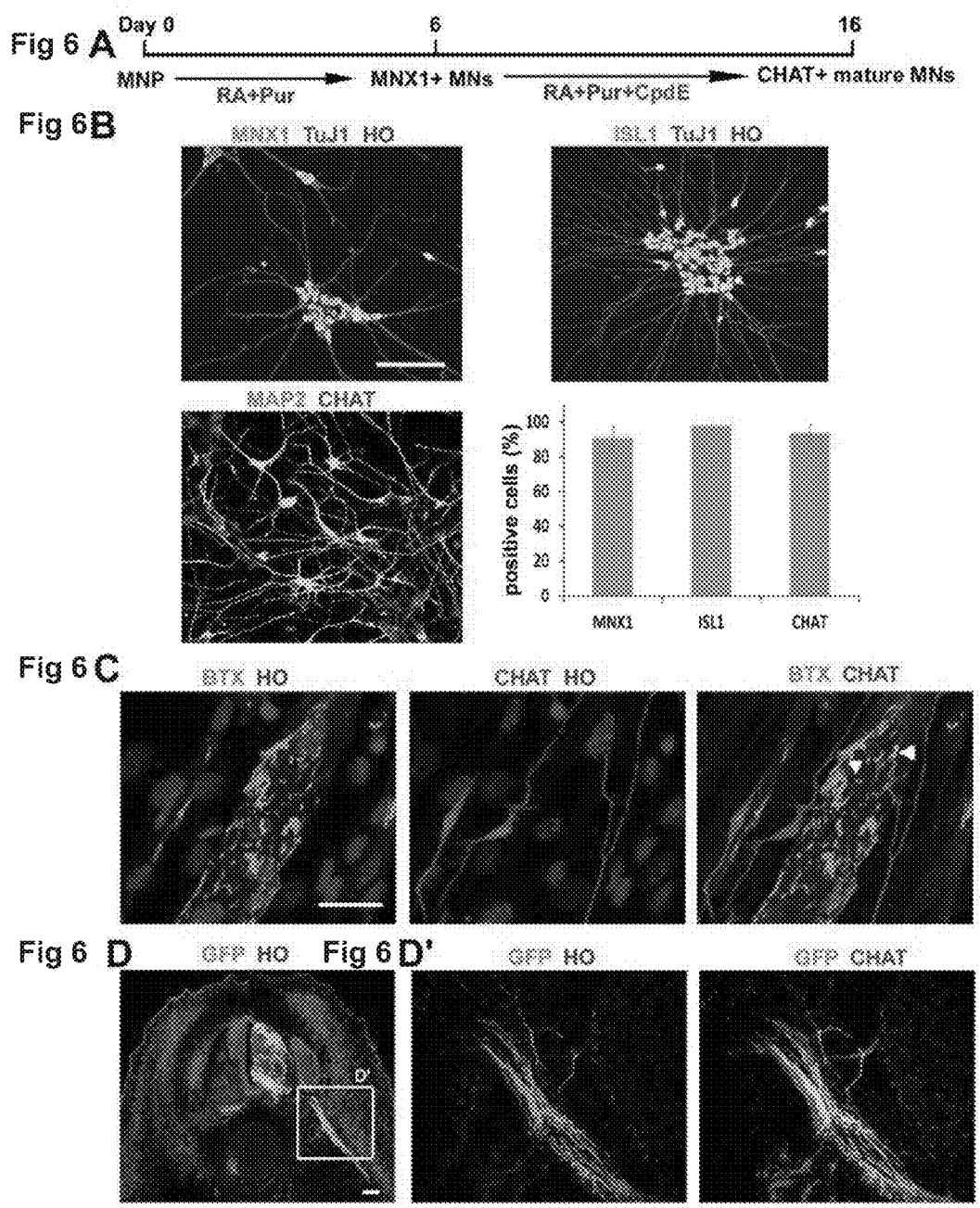
Figure 6A-D'

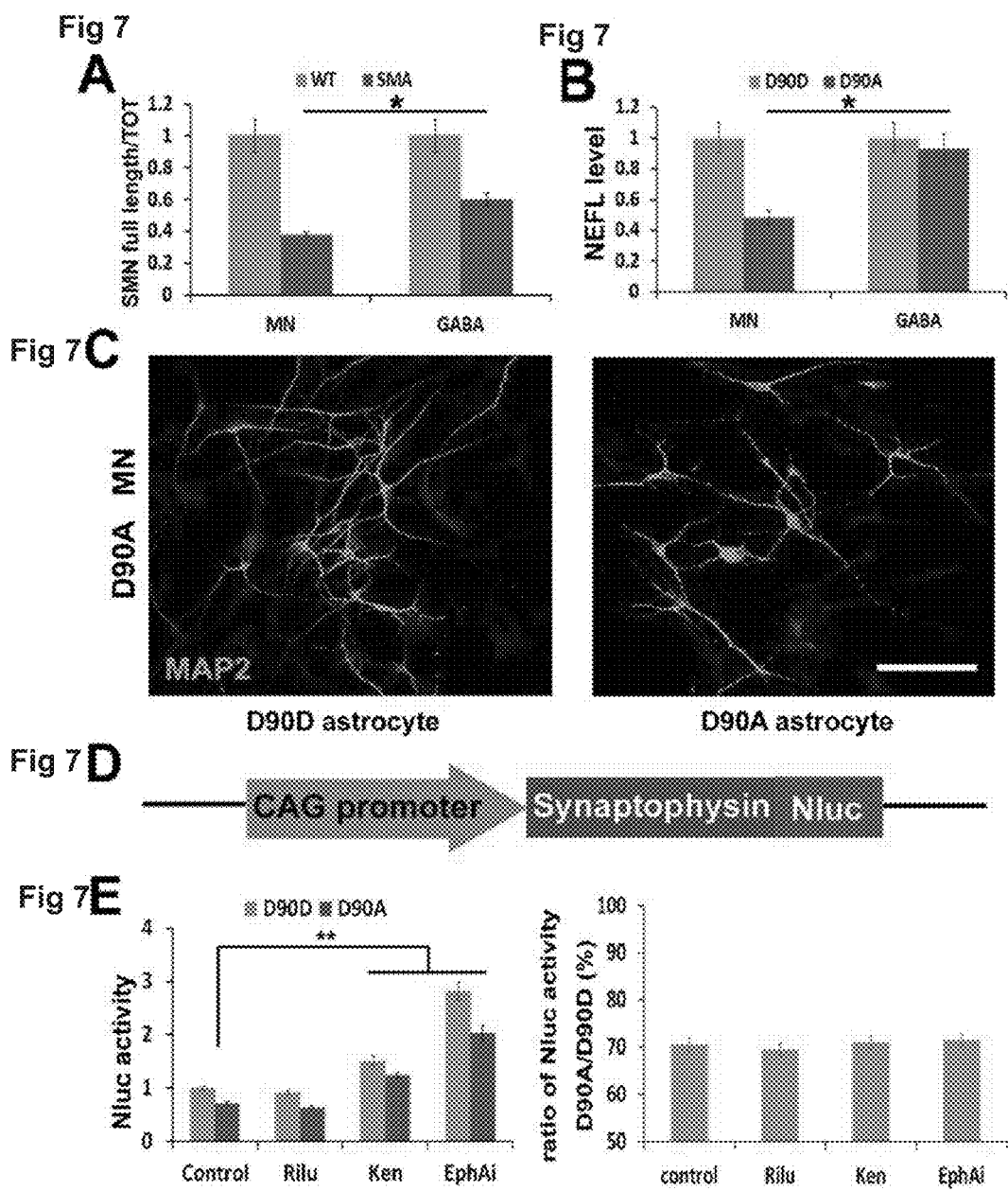
Figure 7A-E

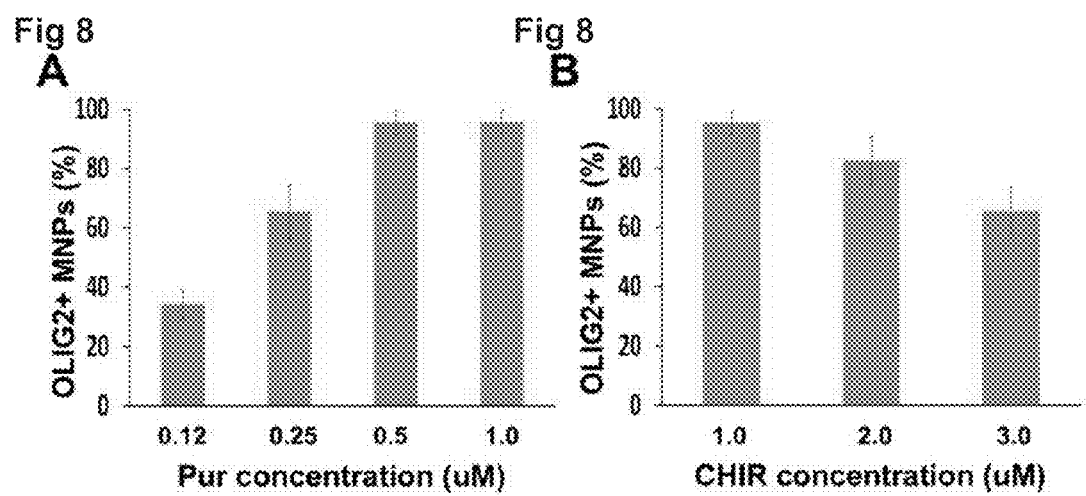
Figure 8A-B

Fig 9A
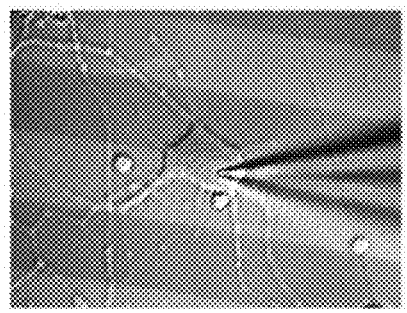
Fig 9B
| Cell size (pF) | 43.3 ± 4.1 |
| RMP (mV) | − 53 ± 2 |
| Rin (MΩ) | 436 ± 112 |
Fig 9C
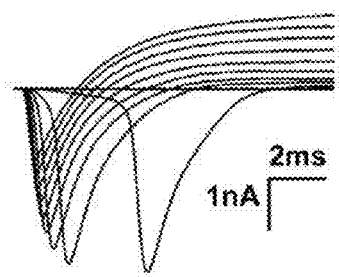
Fig 9D
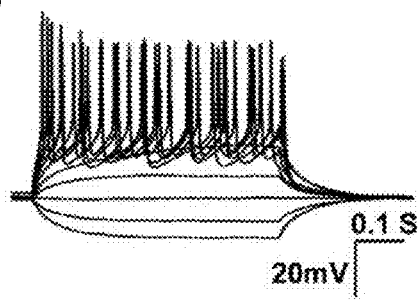
Fig 9E Biocytin
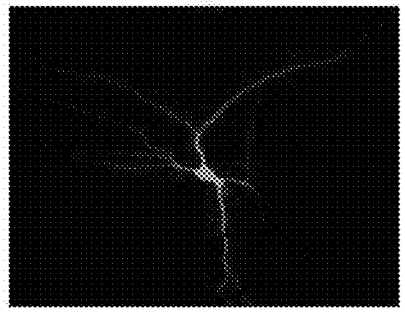
Biocytin CHAT
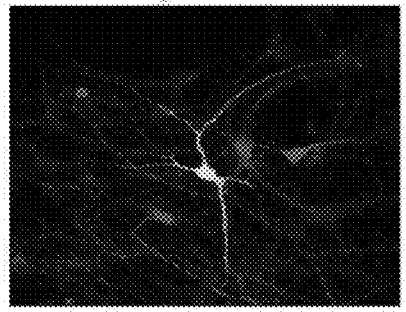
Figure 9A-E

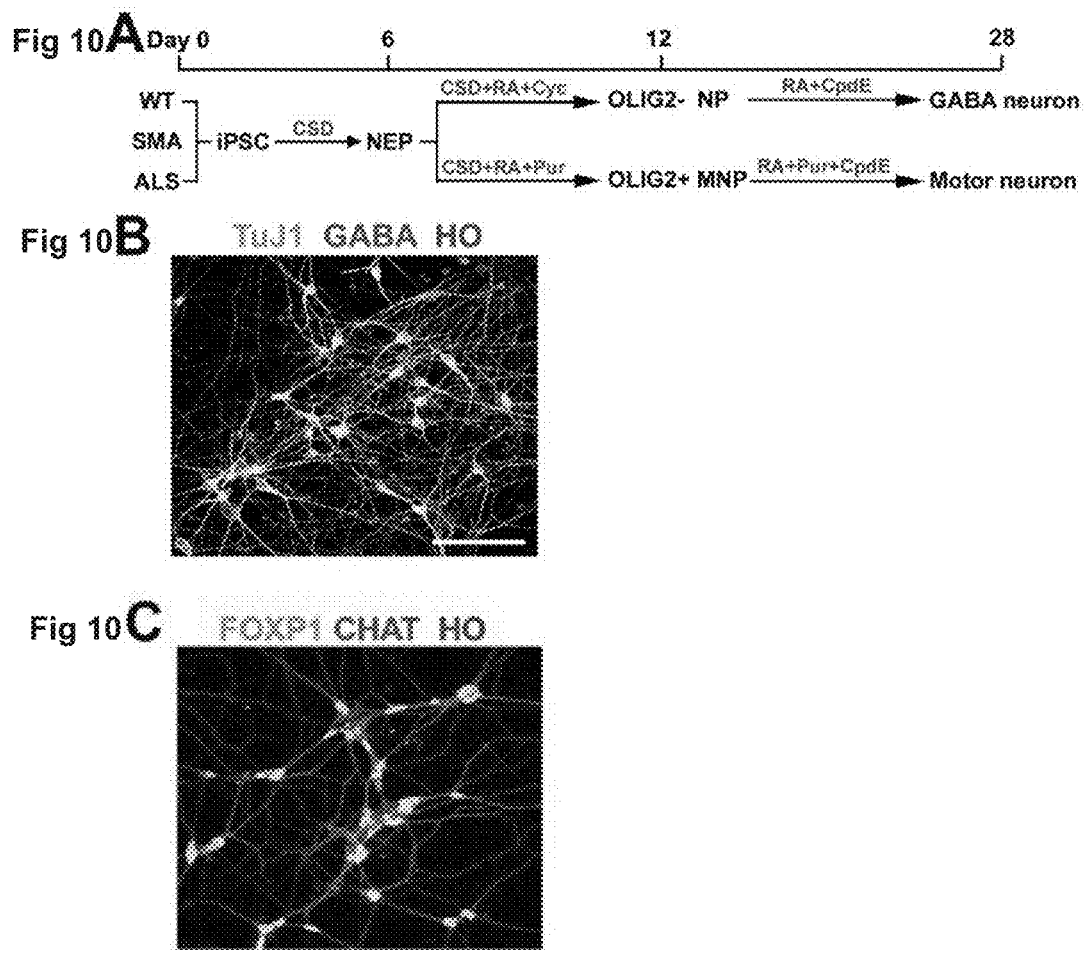
Figure 10A-C

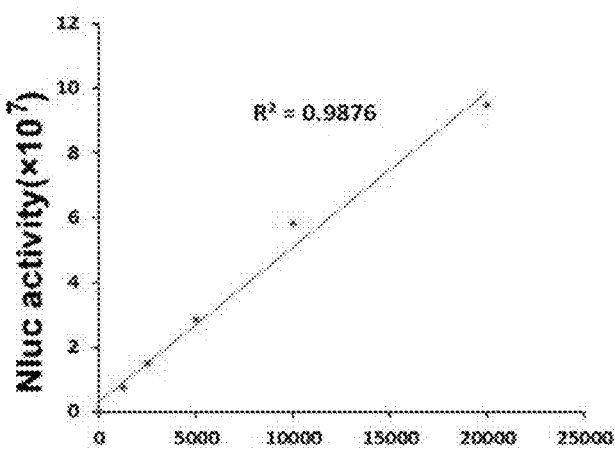
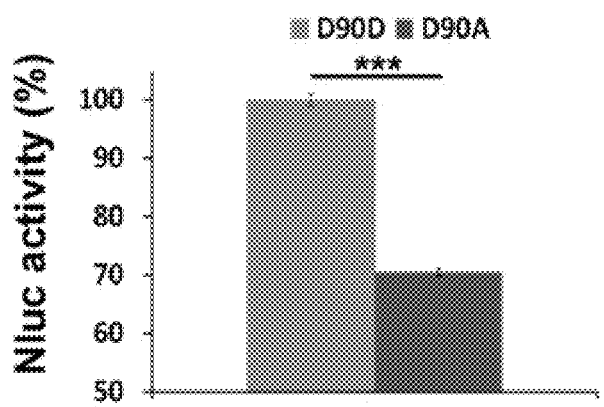
Figure 12A-B

METHODS OF MAINTAINING, EXPANDING AND DIFFERENTIATING NEURONAL SUBTYPE SPECIFIC PROGENITORS

CROSS-REFERENCE TO RELATED APPLICATIONS

This application is a CIP claiming the benefit of U.S. provisional application 62/112,441 filed Feb. 5, 2015 and U.S. Ser. No. 14/194,130, filed Feb. 28, 2014, which claims the benefit of U.S. Provisional Patent Application No. 61/771,572, filed Mar. 1, 2013, all of which are incorporated herein by reference as if set forth in their entirety.

STATEMENT REGARDING FEDERALLY SPONSORED RESEARCH OR DEVELOPMENT

This invention was made with government support under NS074189 awarded by the National Institutes of Health. The government has certain rights in the invention.

FIELD OF THE INVENTION

The present invention relates to methods of expanding the population of neuronal subtype specific progenitors differentiated from human pluripotent stem cells, such as spinal motor neuron progenitors and hindbrain serotonergic neuron progenitors. In particular, the present invention relates to methods of maintaining the regional identity and differentiation potential of neuronal subtype specific progenitors during expansion.

BACKGROUND OF THE INVENTION

The mammalian central nervous system is a complex neuronal network consisting of a diverse array of cellular subtypes generated in a precise spatial and temporal pattern throughout development. Each neuronal subtype within a particular region of the brain and spinal cord carries a unique set of neurotransmitters and establishes connections with its own targets. It is the diversity in molecular and morphological characteristics of neurons which underlies neural circuit formation.

Extrinsic signals provide neuronal progenitors in the forming neural tube with positional identity, such that distinct types of neuronal progenitors express a unique combination of transcription factors. This transcriptional code determines neural progenitor identity. As progenitors differentiate, they generate distinct neuronal subtypes that are also characterized by transcriptional codes and secretion of specific transmitters. For example, motor neurons (MNs) are a highly specialized class of neurons that reside in the spinal cord and project axons in organized and discrete patterns to muscles to control their activity. Motor neurons secrete the transmitter acetylcholine, express transcription factors including MNX1 (also known as HB9), ISL1, and LHX3, and are derived from motor neuron progenitors which express the basic helix-loop-helix (bHLH) transcription factor OLIG2. During neurogenesis, OLIG2 is expressed by MNPcells and is required for the generation of MNs, while the homeodomain protein NKX2.2 is expressed in p3 progenitors and induces V3 neurons. Dessaud et al., *Development* 135:2489-2503 (2008). The most prominent MN diseases are spinal muscular atrophy (SMA) and amyotrophic lateral sclerosis (ALS), in which MNs perish in the disease. For review, see Kanning et al., *Annu. Rev. Neurosci.* 33:409-410 (2010). Similarly, hindbrain serotonin neuronal progenitors express NKX2.2 together with GATA2 but not OLIG2 or PHOX2b and generate serotonin-secreting neurons that project to the entire brain and spinal cord. Numerous psychiatric disorders involve dysfunctional serotonin neurons. For review, see Gordis & Rohrer, *Nat. Rev. Neurosci.* Vol. 3(7):531-541 (2002); Kiyasova & Gaspar, *Eur. J. Neurosci.* Vol. 34(10):1553-1562, (2011).

Neural progenitor cells have been expanded in culture in the presence of mitogens such as epidermal growth factor (EGF) and/or fibroblast growth factor 2 (FGF2). For review, see Weiss et al., *Trends Neurosci.* Vol. 19:387-393 (1996). Neural progenitors expanded under such conditions exhibit diminished potential for generating neurons over glial cells. See Temple, *Nature* Vol. 414:112-117 (2001). This trend is in general agreement with the shift from neurogenesis to gliogenesis observed during normal development. Embryonic ventral mesencephalic progenitors, which produce robust dopaminergic neurons at the time of isolation, lose their dopaminergic potential shortly after expansion in the presence of FGF2. See Studer et al., *Nat. Neurosci.* Vol. 1:290-295 (1998). Similarly, human embryonic stem cell (ESC)-derived neural progenitors retain their positional identity, as determined by homeodomain transcription factor expression, and a high degree of neurogenic potential even after months of expansion. See Zhang et al., *J. Hematother. Stem Cell Res.* Vol. 12:625-634 (2003). The potential to produce large projection neurons such as midbrain dopamine neurons, spinal cord motor neurons, and hindbrain serotonergic neurons, however, fades within two to four passages and is replaced by other neuronal populations. This phenomenon creates a barrier for producing consistent populations of neuronal progenitors with predictable differentiation potential and functional properties. Accordingly, there remains a need for compositions and methods for expanding neuronal progenitors while maintaining the differentiation potential of the progenitors to yield the predicted array of diverse neuronal subtypes.

SUMMARY OF THE INVENTION

In one aspect, the present invention provides a method for maintaining a population of neuronal subtype-specific progenitors. Typically, the method does not require cell sorting. The method can comprise culturing neuronal subtype-specific progenitors in a culture medium comprising a Wnt signaling pathway agonist, an inhibitor of the Bone Morphogenetic Protein (BMP) signaling pathway, an inhibitor of the transforming growth factor beta (TGFβ) signaling pathway, and a Notch signaling pathway agonist whereby expression of a neuronal subtype-specific progenitor gene expression profile is maintained in the neuronal subtype-specific progenitors. The neuronal subtype-specific progenitors can have a gene expression profile comprising expression of at least one of SOX1, SOX2, NESTIN, N-Cadherin, and Ki67. The neuronal subtype-specific progenitors can be spinal neural progenitors having a gene expression profile further comprising expression of at least one of HOXA5 and HOXB8, and substantially no expression of midbrain, hindbrain, or forebrain markers. The spinal neural progenitors can be OLIG2[+] spinal motor neuron progenitors.

The neuronal subtype-specific progenitors can be hindbrain neural progenitors having a gene expression profile further comprising expression of at least one of GBX2, KROX20, HOXA1-4, and HOXB1-4, and substantially no expression of forebrain, spinal cord, or midbrain markers. The hindbrain neural progenitors can be NKX2.2[+] hindbrain serotonergic neural progenitors.

In some cases, the neuronal subtype-specific progenitors are midbrain neural progenitors having a gene expression profile further comprising expression of at least one of EN1 and EN2, and substantially no expression of forebrain, spinal cord, or hindbrain markers. The midbrain neural progenitors can be LMX1A+ midbrain dopaminergic neuron progenitors.

The neuronal subtype-specific progenitors can be forebrain neural progenitors having a gene expression profile further comprising expression of at least one of FOXG1 and OTX2, and substantially no expression of midbrain, spinal cord, or hindbrain markers. The forebrain neural progenitors can be NKX-2.1+ forebrain GABAergic neuron progenitors.

The Wnt signaling pathway agonist can be a GSK3 inhibitor selected from the group consisting of CHIR99021 and 6-bromo-iridium-3'-oxime. The BMP signaling pathway inhibitor can be selected from the group consisting of DMH-1, Dorsomorphin, and LDN-193189. The Notch signaling pathway agonist can be a histone deacetylase (HDAC) inhibitor selected from the group consisting of valproic acid (VPA), suberoyl bis-hydroxamic acid (SAHA), and sodium butyrate. The TGFβ signaling pathway inhibitor can be selected from the group consisting of SB431542, SB505124, and A83-01. The culture medium can comprise CHIR99021, DMH-1, SB431542, and VPA. The culture medium can comprise between about 1 μM-3 μM CHIR99021; about 1 μM-5 μM DMH-1; about 1 μM-5 μM SB431542; and about 0.2-mM-2 mM VPA.

The neuronal subtype specific progenitors can be OLIG2+ spinal motor neuron progenitors, where the culture medium comprises CHIR99021, DMH-1, SB431542, VPA, a SHH pathway agonist, and a RA pathway agonist. The SHH pathway agonist can be selected from the group consisting of purmorphamine and SAG (Smoothened Agonist). The RA pathway agonist can be retinoic acid. The culture medium can comprise between about 1 μM to 3 CHIR99021; about 1 μM to 5 μM DMH-1; about 1 μM to 5 μM SB431542; about 0.2 mM-2 mM VPA; and about 0.1 μM to 1 μM purmorphamine; about 0.01 μM to 1 μM RA. The OLIG2+ spinal motor neuron progenitors can be maintained in a culture substantially free of MNX1+ post-mitotic motor neurons for at least 5 weeks. The OLIG2+ spinal motor neuron progenitors can be maintained in a culture substantially free of MNX1+ post-mitotic motor neurons for at least 10 weeks.

The neuronal subtype specific progenitors can be NKX2.2+ hindbrain serotonergic neural progenitors, where the culture medium comprises CHIR99021, DMH-1, SB431542, VPA, and purmorphamine. The culture medium can comprise about 1 μM to 3 μM CHIR99021; about 1 μM to 5 μM DMH-1; about 1 μM to 5 μM SB431542; about 0.2 mM-2 mM VPA; and about 0.1 μM to 1 μM purmorphamine. The NKX2.2+ hindbrain serotonergic neural progenitors can be maintained substantially free from differentiation for at least 5 weeks. The NKX2.2+ hindbrain serotonergic neural progenitors can be maintained substantially free from differentiation for at least 10 weeks.

In some cases, neuronal subtype specific progenitors are obtained from pluripotent stem cells. The pluripotent stem cells can be human pluripotent stem cells. The human pluripotent stem cells can be human embryonic stem cells or human induced pluripotent stem cells. The neuronal subtype specific progenitors can be obtained from a human embryo.

In another version, the present invention is a method of generating populations of motor neuron progenitor cells from stem cells, comprising the steps of (a) culturing pluripotent stem cells in a culture medium comprising a Wnt signaling pathway agonist, a BMP signaling pathway inhibitor, and a TGFβ signaling inhibitor, wherein a population of at least at least 90%, preferably 95%, more preferably 98%, pure Sox1+/Hoxa3+ neural stem cells is obtained, and (b) culturing the neural stem cells of step (a) in a medium additionally comprising retinoic acid and purmorphamine, wherein a population of at least 85%, preferably 90%, more preferably 95%, pure Olig2+/Nkx2.2− motor neuron progenitor cells is obtained.

In a preferred version, the concentration of the Wnt signaling pathway agonist is decreased in step (b) relative to step (a). In another preferred version, the Wnt signaling pathway agonist is a GSK3 inhibitor selected from the group consisting of CHIR99021 and 6-bromo-iridium-3'-oxime. In a preferred version, the BMP signaling pathway inhibitor is selected from the group consisting of DMH-1, Dorsomorphin, and LDN-193189. In a preferred version, the TGFβ signaling inhibitor is selected from the group consisting of SB431542, SB505124, and A83-01. In a preferred version, the concentration of Wnt signaling pathway agonist CHIR99021 is 3 μM (+/−10%) in step (a) and 1 μM (+/−10%) in step (b).

In a preferred version, the method further comprises step (c), culturing the motor neuron progenitor cells of step (b) in a medium comprising retinoic acid, purmorphamine and a Notch signaling inhibitor, wherein a population of at least 80% pure MNX1+/ChAT+ motor neurons is obtained. Preferably, the Notch inhibitor is selected from the group consisting of Compound E, DAPT, and DBZ.

In a preferred method, a single MNP has been expanded by a factor of at least $1 \times 10^4$.

In another version of the invention, the method further comprises the step of culturing the motor neuron progenitor cells of step (b) in a medium comprising retinoic acid, purmorphamine and a Notch signaling inhibitor, wherein a population of at least 80%, preferably at least 85%, more preferably at least 90% pure MNX1+/ChAT+ motor neurons is obtained.

In another version, the present invention is a population of cells as described above. In one version of the invention, the population is Sox1+/Hoxa3+ caudal neural stem cells obtained by the method described above. In another version, the population is Olig2+/Nkx2.2− motor neuron progenitor cells obtained by the method described above. In another version, the population is MNX1+/ChAT+ motor neuron cells obtained by the method described above. Preferably, these cells exhibit formation of neuromuscular junctions when co-cultured with skeletal muscle cells and projection of axons toward muscles when grafted into the developing chick spinal cord.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing in color. Copies of this patent or patent application publication with color drawings will be provided by the Office upon request and payment of the necessary fee.

FIG. 4 A-D discloses generation of pure population of OLIG2$^+$ MNPs from hPSCs. (FIG. 4A) Schematics showing the time course and small molecule cocktail for hPSC differentiation into MNPs. (FIG. 4B) The regional identity (OTX2+ vs. HOXA3+) and quantitation of SOX1+ NEPs after 6 days of culture in CHIR+SB+DMH-1 vs. SB+DMH-1 condition. Scale bars: 50 µm. (FIG. 4C) CHIR+SB+DMH-1+RA+Pur cocktail induced pure MNPs at Day 12, which express OLIG2 (green) but not NKX2.2 (red). Quantification is shown on right. Scale bars: 50 µm. (FIG. 4D) The efficiency of OLIG2$^+$ MNP differentiation from multiple hPSC lines.

FIG. 5 A-E shows the expansion of OLIG2$^+$ MNPs. (FIG. 5A) RA and Pur are required for maintaining the identity of MNPs with OLIG2 (green) expression, by preventing a switch to NKX2.2$^+$ (red) progenitors. Scale bars: 50 µm. (FIG. 5B) CHIR+SB+DMH-1 are required for maintaining the proliferation of MNPs with Ki67 (red) expression at the maximum level. Scale bars: 50 µm. (FIG. 5C) Schematics showing the expansion of MNPs with the combination of small molecules. (FIG. 5D) The MNPs were expanded for at least 5 passages yet maintained the OLIG2 (green) expression. (FIG. 5E) Cumulative hPSC-derived MNP counts over five passages (passages denoted p1-p5).

FIG. 6 A-D presents MNPs differentiating into enriched functional MNs. (FIG. 6A) Schematics showing the time course and small molecule cocktail for MNP differentiation into mature MNs. (FIG. 6B) Quantification of MNX1$^+$ and ISL1$^+$ (green) MNs on Day 6, and CHAT$^+$ (red) mature MNs on Day 16. Scale bars: 50 µm. (FIG. 6C) MNs, stained with CHAT antibody (red), formed neuromuscular junctions, labeled with bungarotoxin (BTX, green), when co-cultured with myotubes. Scale bars: 100 µm. (FIG. 6D) Representative image of xenotransplantation of GFP labeled human MNs into a developing chicken embryo. Scale bars: 50 µm. (FIG. 6D') magnification of the field showing that human MN axons (GFP$^+$/CHAT$^+$) projected ventrally through the ventral roots.

FIG. 7 A-D shows enriched MNs enable presentation of disease phenotypes and building of screening platforms. (FIG. 7A) SMA MNs exhibited a lower (38±4%) proportion of full-length SMN among total SMN mRNA than that in SMA GABA neurons (60±6%), when comparing to wild type (WT) neurons (*$p<0.05$). (FIG. 7B) ALS (D90A) MNs exhibited 45±4% reduction of NEFL mRNA than that in ALS GABA neurons, when comparing to corrected (D90D) neurons (*$p<0.05$). (FIG. 7C) ALS (D90A) MNs showed neurite fragmentation and reduced neurite length when culturing on ALS (D90A) astrocytes, comparing to that on corrected (D90D) astrocytes. Scale bars: 50 µm. (FIG. 7D) Schematic of SYP-Nluc reporter. (FIG. 7E) Quantification of Nluc activity (left panel) and ratio (right panel) of SYP-Nluc reporter MNs on ALS (D90A) and corrected (D90D) astrocytes, when comparing between the control, Riluzole (Rilu), Kenpaullone (Ken) and EphA inhibitor (EphAi) groups (**$P<0.01$).

FIG. 8 A-B is the serial titration of Pur and CHIR concentration. In combination with 0.1 µM RA, 2 µM SB and 2 µM DMH-1, Pur concentration varied from 0.12 µM to 1 µM (FIG. 8A), and CHIR concentration varied from 1 µM to 3 µM (FIG. 8B). OLIG2$^+$ MNPs were quantified under different conditions.

FIG. 9 A-E discloses the electrophysiological characteristics of MNs. (FIG. 9A) Whole-cell patch-clamp recording on a neuron cultured on astrocytes for 28 days. (FIG. 9B) Electrophysiological characteristics, including capacitance, resting membrane potential (RMP) and resistance (Rin). (FIG. 9C) Inward Na+ and outward K+ currents were triggered upon −50 mV to 50 mV voltage steps. (FIG. 9D) Action potentials were induced from −40 pA to 100 pA injected current steps. (FIG. 9E) Immunocytochemistry reveals the recorded cells (identified by biocytin back-fill) to be CHAT positive.

FIG. 10 A-C shows the generation of MNs and GABA+ non-MNs from human iPSCs. (FIG. 10A) Schematics showing the time course and small molecule cocktail for hiPSCs differentiation into MNs and GABA neurons. Cyc is an SHH antagonist. Repression of SHH signaling induces the dorsal GABA neuron. Immunofluorescent images of GABA$^+$ neurons (FIG. 10B) and CHAT$^+$ MNs (FIG. 10C) on Day 28. Scale bars: 50 µm. The term CSD stands for three small molecules—CHIR99021, SB431542, and DMH1.

FIG. 12 A-B discloses the SYP-Nluc reporter assay. (FIG. 12A) The linear relationship between Nluc activity and MN number. (FIG. 12B) The Nluc activity of SYP-Nluc MNs was lower when co-cultured on D90A astrocytes, comparing to that on D90D astrocytes (***$P<0.001$).

DETAILED DESCRIPTION OF THE INVENTION

Figure 1:
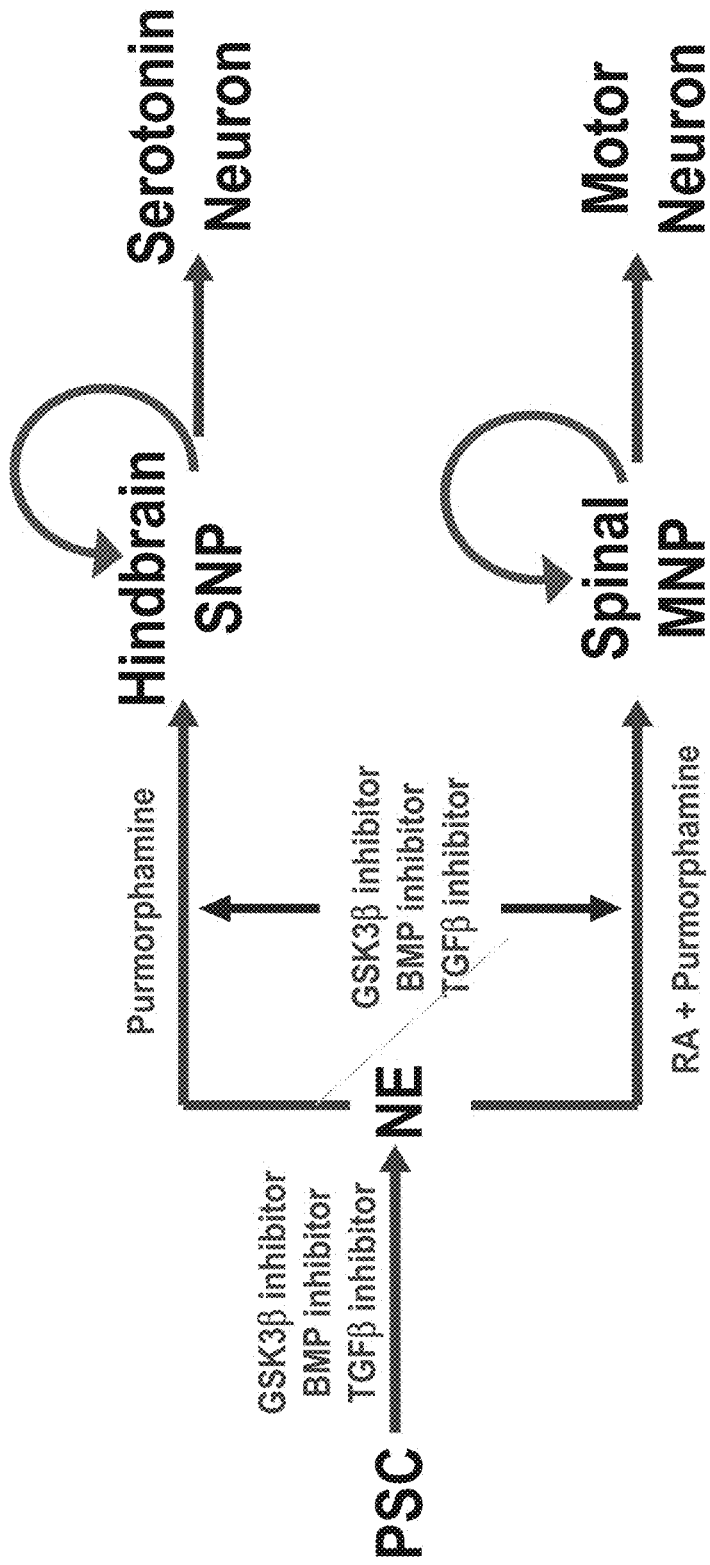
FIG. 1 is a flow chart depicting differentiation of spinal motor neuron progenitors and hindbrain serotonergic neuron progenitors from pluripotent stem cells and expansion of these neuronal progenitors under specified conditions. Abbreviations: PSC (pluripotent stem cell); NE and NEP (neuroepithelial progenitor); MNP (motor neuron progenitor); SNP (serotonergic neural progenitor); RA (retinoic acid); MN (motor neuron). The curved arrows indicate an expanded or maintained population.
Figure 2:
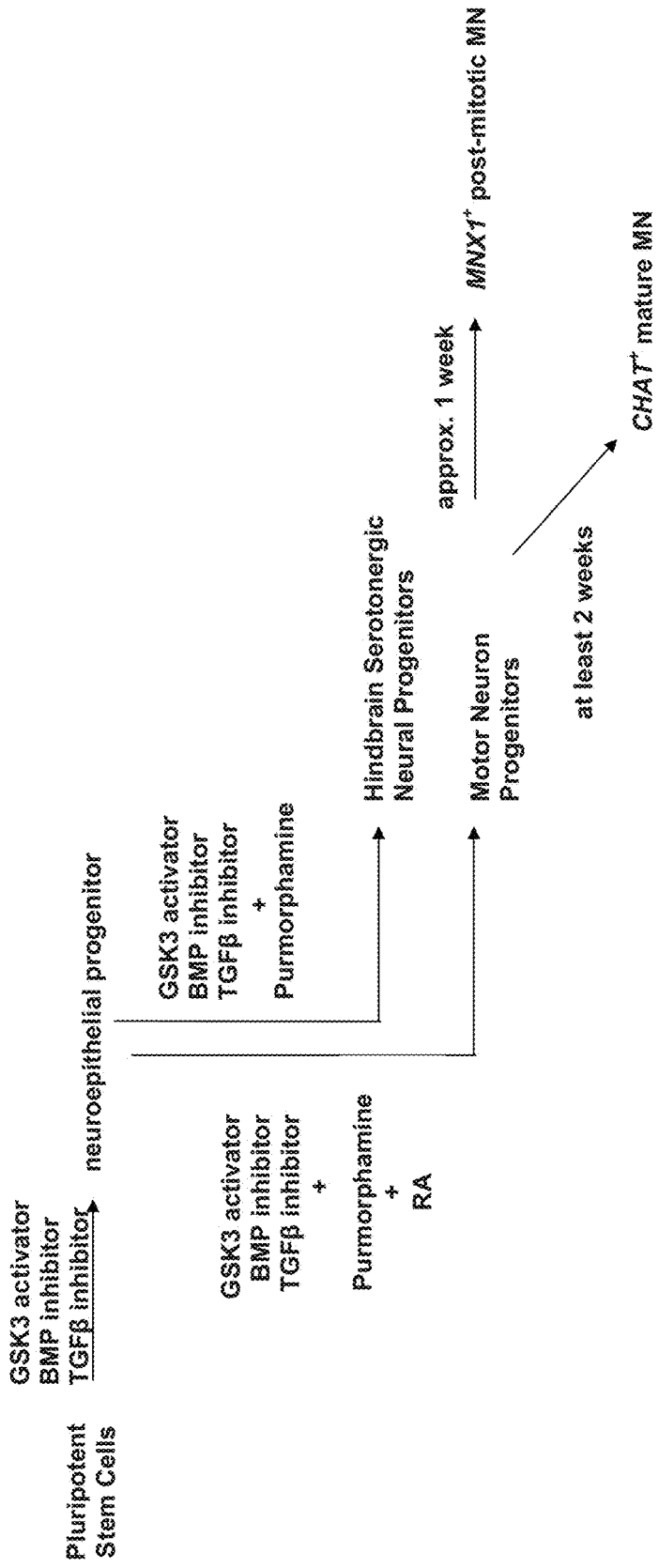
FIG. 2 is a flow chart depicting an exemplary protocol for differentiating mature motor neurons from an expanded population of spinal motor neuron progenitors. MN (motor neuron.)

The present invention is based, at least in part, on the inventors' discovery that a defined cocktail of small molecules or chemical compounds could be used to maintain the proliferation of neuronal subtype-specific progenitor cells, such as spinal motor neuron progenitors and hindbrain serotonergic neuron progenitors differentiated from human pluripotent stem cells. The inventors further discovered that certain culture conditions could maintain in vitro cultured neuronal subtype-specific progenitor cells in their progenitor state with substantially no loss of differentiation potential. Upon providing a differentiation condition to the maintained, expanded progenitors, the Inventors induced differentiation of the progenitors into, for example, mature motor neurons and serotonergic neurons.

Methods of Generating and Maintaining Neuronal Subtype-Specific Progenitors

In one aspect, therefore, the present invention is directed to methods for generating and maintaining a population of neuronal subtype specific progenitors. Neuronal subtype-specific progenitors can include, without limitation, forebrain neural progenitors, spinal neural progenitors, hindbrain neural progenitors, and midbrain neuron progenitors. The phenotype of a neuronal subtype specific progenitor is specified by the expression of unique combination of transcription factors in rostral-caudal and dorsal-ventral patterns. For example, forebrain neural progenitors can be NKX-2.1$^+$ forebrain GABAergic neuron progenitors, and midbrain neural progenitors can be LMX1A$^+$ midbrain dopaminergic neuron progenitors.

A method for generating a population of neuronal subtype-specific progenitors can include culturing neuroepithelial cells in a culture medium comprising a Wnt signaling pathway agonist, an inhibitor of the bone morphogenetic protein (BMP) signaling pathway, an inhibitor of the transforming growth factor beta (TGFβ) signaling pathway, and Notch signaling pathway agonist, and at least one of retinoic acid (RA) or a sonic hedgehog (SHH) pathway agonist, where the cells are cultured for a time sufficient to induce expression of a neuronal subtype-specific progenitor gene expression profile. A neuronal subtype-specific gene expression profile will include expression of at least one of SOX1, SOX2, NESTIN, N-Cadherin, and Ki67. In the case of hindbrain neural progenitors, the gene expression profile can further include at least one of GBX2, KROX20, HOXA1-4, and HOXB1-4, but substantially no expression of forebrain, spinal cord, or midbrain markers. In an exemplary embodiment, a hindbrain neural progenitor is a NKX2.2$^+$ hindbrain serotonergic neural progenitor. For midbrain neural progenitors, the gene expression profile can further include at least one of EN1, LMX1A, and LMX1B but substantially no expression of forebrain, spinal cord, or hindbrain markers. In some cases, a midbrain neural progenitor is a LMX1A$^+$ midbrain dopaminergic neuron progenitor. For forebrain neural progenitors, the gene expression profile can further include at least one of FOXG1, OTX2, EMX1, NKX2.1, and SIX3, but substantially no expression of midbrain, spinal cord, or hindbrain markers. In some cases, the forebrain neural progenitor is a NKX-2.1$^+$ forebrain GABAergic neuron progenitor. For a spinal neural progenitor, the gene expression profile can further include at least one of HOXB6 and HOXB8, but substantially no expression of midbrain, hindbrain, or forebrain markers. In some cases, the spinal neural progenitor is a OLIG2$^+$ spinal motor neuron progenitor.

In some cases, a method for generating neuronal subtype-specific progenitors can further comprise culturing pluripotent stem cells in a culture medium for a time sufficient to induce differentiation of the pluripotent stem cells into neuroepithelial cells. The culture medium can comprise (i) a Wnt signaling pathway agonist, (ii) an inhibitor of the BMP signaling pathway, and (iii) an inhibitor of the TGFβ signaling pathway. Pluripotent stem cells that can be used include human pluripotent stem cells such as human embryonic stem cells and human induced pluripotent stem cells.

Methods of maintaining a population of neuronal subtype specific progenitors derived from pluripotent stem cells can comprise culturing neuronal subtype specific progenitors in a culture medium comprising a Wnt signaling pathway agonist, an inhibitor of the bone morphogenetic protein (BMP) signaling pathway, an inhibitor of the transforming growth factor beta (TGFβ) signaling pathway, and a Notch signaling pathway agonist. In some cases, such a culture medium is called a maintenance culture medium. By "maintaining" a population of neuronal subtype-specific progenitors, we mean maintenance of a phenotype of a unique gene expression profile (e.g., profile of transcription factors expressed in a given cell type) characteristic of a given neuronal subtype specific progenitor. As used herein, the term "maintaining" refers to maintenance of such a phenotype (e.g., cell morphology, gene expression profile) characteristic of a given neuronal subtype specific progenitor for at least 5 passages or at least 5 weeks, preferably at least 8 passages or at least 8 weeks, and most preferably at least 10 passages or at least 10 weeks.

A culture medium comprising small molecule agonists of each of the Wnt and Notch signaling pathways, and small molecule inhibitors of the transforming growth factor beta (TGFβ) and BMP pathways is required for maintaining the proliferation and self-renewal of neuronal progenitors generally. However, other small molecules or patterning factors are additionally required for maintaining the unique gene expression profile characteristic of a neuronal subtype specific progenitor. For example, a Sonic Hedgehog (SHH) signaling pathway agonist (e.g., purmorphamine) and a retinoic acid (RA) signaling pathway agonist are additionally required to maintain expression of the transcription factor OLIG2 in motor neuron progenitors and to maintain motor neuron progenitor identity and differentiation capacity. Similarly, a SHH signaling pathway agonist is additionally required to maintain expression of the transcription factor NKX2.2 in hindbrain serotonergic neuron progenitors and to maintain hindbrain serotonergic neuron progenitor identity and differentiation capacity.

In an exemplary embodiment, a culture medium for maintaining a population of any type of other neuronal subtype specific progenitors according to a method provided herein comprises RA, purmorphamine, the GSK3 inhibitor CHIR99021, the BMP signaling inhibitor DMH-1, and the TGFβ signaling inhibitor SB431542. In some cases, the culture medium further comprises between about 0.1 µM to 1.0 µM RA, and between about 0.1 µM to 1.0 purmorphamine.

In other cases, maintaining neuronal progenitors according to a method provided herein can include providing the cells with a culture medium comprising an agonist of Notch signaling such as, for example, VPA (Valproic acid). VPA is available from several commercial chemical compound vendors (e.g., Tocris Bioscience, Sigma-Aldrich). VPA is an HDAC inhibitor which can indirectly activate Notch signaling. Stockhausen et al., Br. J. Cancer. Vol. 92(4):751-759 (2005). Other small molecule inhibitors of HDAC which can be used to activate Notch signaling include, for example, suberoyl bis-hydroxamic acid (SAHA) and sodium butyrate. Accordingly, a culture medium appropriate for use in a method for maintaining neuroepithelial cells can comprise CHIR99021, DMH-1, SB431542, and at least one of valproic acid (VPA), a SHH pathway agonist, and RA (or RA pathway agonist). In some cases, the culture medium can comprise between about 1 µM-3 µM CHIR99021, between about 1 µM-5 µM DMH-1, between about 1 µM-5 µM SB431542, and at least one of between about 0.2 mM-2 mM VPA, between about 0.2 µM-2 µM RA, and between about 0.2 µM-2 µM purmorphamine.

Any appropriate culture method can be used to practice a method provided herein. In an exemplary embodiment, adherent culture methods can be used. Adherent culture (or "colony culture") allows direct visualization of neural differentiation, including the formation of neural tube-like rosettes during neuroepithelial induction and the migration of neuroepithelial cells. Adherent/colony culture permits ready removal of non-neural colonies and promotes subsequent neural differentiation. In some cases, suspension culture can be used for initially separating pluripotent cells from mouse embryonic fibroblast (MEF) feeder cells or for purifying neuroepithelial cells.

Methods of Generating and Maintaining Motor Neuron Progenitors

In another aspect, the present invention is directed to methods for generating motor neuron progenitors and methods for maintaining an expanded population of motor neuron progenitors. As used herein, the term "motor neuron progenitor" refers to a progenitor or precursor cell which will mature, or is capable of maturing, into a motor neuron, wherein the MNPs express Olig2 but do not express NkX2.2.

To generate motor neuron progenitors, a first step in the method can be to generate a population of neuroepithelial cells. Neuroepithelial cells are also known as neural stem cells, and the terms "neuroepithelial cell" and "neural stem cell" are used interchangeably throughout. A method for generating a population of motor neuron progenitors can comprise culturing human pluripotent stem cells in a culture medium comprising a Wnt signaling pathway agonist, an inhibitor of the BMP signaling pathway, and an inhibitor of the TGFβ signaling pathway for a time sufficient to induce differentiation of pluripotent stem cells into neuroepithelial cells. Pluripotent stem cells useful for the methods provided herein include human embryonic stem cells (hESCs) and human induced pluripotent stem cells (hIPS cells).

In some cases, a culture medium appropriate for generating a population of neuroepithelial cells can comprise a plurality of small molecules or other chemical compounds which promote the differentiation of pluripotent stem cells into neuroepithelial cells. In some cases, such a culture medium is called a differentiation culture medium. The plurality of small molecules or chemical compounds can include an agonist of the canonical Wnt signaling pathway, an inhibitor of the BMP signaling pathway, and an inhibitor of TGFβ signaling. For example, a method for generating a population of neuroepithelial cells can include providing pluripotent stem cells with a culture medium comprising CHIR99021, a GSK3 inhibitor. By inhibiting GSK3, CHIR99021 activates the canonical Wnt signaling pathway. CHIR99021 has been reported to inhibit the differentiation of mouse and human embryonic stem cells (ESCs) through Wnt signaling. For review, see Wray and Hartmann, *Trends in Cell Biology* 22:159-168 (2012). Another GSK3 inhibitor which can be used is, for example, the Wnt/β-catenin signaling agonist 6-bromo-iridium-3'-oxime ("BIO"). See Meijer et al., *Chem. Biol.* 10(12):1255-66 (2003). GSK3 inhibitors such as those described herein are available from commercial vendors of chemical compounds (e.g., Selleckchem, Tocris Bioscience).

In some cases, an inhibitor of BMP signaling is DMH-1, which blocks BMP signaling by inhibiting Activin receptor-like kinase (ALK2). Other small molecule inhibitors of Activin receptor-like kinases which can be used to block BMP signaling include, for example, Dorsomorphin and LDN-193189. Both compounds affect Smad-dependent and Smad-independent BMP signaling triggered by BMP2, BMP6, or GDF5. Boergermann et al., *Int. J. Biochem. Cell Biol.* 42(11): 1802-7 (2010).

In some cases, an inhibitor of TGFβ signaling is SB431542, which inhibits Activin receptor-like kinases 4, 5, and 7 (ALK4, ALK5, and ALK7). SB431542 can be purchased from any one of several commercial chemical compound vendors (e.g., Tocris Bioscience, Sigma-Aldrich). By inhibiting Activin receptor-like kinases 4, 5, and 7, SB431542 inhibits TGFβ signaling. Other small molecule inhibitors of Activin receptor-like kinase 5 (ALK5) (also known as transforming growth factor-α type I receptor kinase) such as SB505124 and A83-01 can be used to inhibit TGFβ signaling.

In an exemplary embodiment, a culture medium for use according to a method provided herein comprises the GSK3 inhibitor CHIR99021, the BMP signaling inhibitor DMH-1, and the TGFβ signaling inhibitor SB431542. In some cases, the culture medium can comprise between about 1 μM-3 μM CHIR99021, between about 1 μM-5 μM DMH-1, and between about 1 μM-5 μM SB431542.

In some cases, a culture medium for use according to a method provided herein comprises a basal culture medium supplemented with small molecules or chemical compounds such as those described herein. For example, a culture medium can be Neurobasal® culture medium (Life Technologies. In some cases, a culture medium comprises DMEM/F12, Neurobasal medium at 1:1, 1×N2 neural supplement (N-2 Supplement; Gibco), 1×B27 neural supplement (B-27 Supplement; Gibco), and 1 mM ascorbic acid.

A method for generating motor neuron progenitors can further comprise inducing neuroepithelial cells to differentiate into spinal motor neuron progenitors. In some cases, the method comprises culturing neuroepithelial cells in a culture medium comprising a Wnt signaling pathway agonist, an inhibitor of the BMP signaling pathway, an inhibitor of the TGFβ signaling pathway, a sonic hedgehog (SHH) signaling agonist, and a RA signaling agonist for a time sufficient to induce expression of a motor neuron progenitor marker (OLIG2).

In some cases, generating motor neuron progenitors according to a method provided herein can include providing neuroepithelial cells (e.g., stem cell-derived NE cells) with a culture medium comprising a SHH signaling pathway agonist such as, for example, purmorphamine. Purmorphamine is available from several commercial chemical compound vendors (e.g., Tocris Bioscience, Stemgent). Purmorphamine activates SHH signaling by directly targeting Smoothened ("Smo"), a critical component of the SHH signaling pathway. Sinha et al., *Nature Chem. Biol.* 2:29-30 (2006). Other small molecule agonists of Smo which can be used to activate SHH signaling include, for example, SAG ("Smoothened Agonist"). The hedgehog pathway agonist SAG is a cell-permeable chlorobenzothiophene compound that modulates the coupling of Smo with its downstream effector by interacting with the Smo heptahelical domain. SHH acts in a graded manner to establish different neural progenitor cell populations. See Briscoe et al., *Semin. Cell Dev. Biol.* 10(3):353-62 (1999).

In some cases, generating motor neuron progenitors according to a method provided herein can include providing cells with a culture medium comprising a RA signaling agonist such as RA (e.g., all trans retinoic acid). RA is available from several commercial chemical compound vendors (e.g., Tocris Bioscience, Sigma-Aldrich). RA activates RA signaling by binding nuclear hormone receptors retinoic acid receptors (RARs), which is required for specification of motor neuron progenitors. See Novitch et al., *Neuron* 40(1): 81-95 (2003).

In an exemplary embodiment, a culture medium for generating motor neuron progenitors according to a method provided herein comprises Wnt signaling agonist CHIR99021, BMP signaling inhibitor DMH-1, TGFβ signaling inhibitor SB431542, SHH signaling agonist purmorphamine, and retinoic acid. In some cases, the culture medium comprises between about 1 μM-3 μM CHIR99021, between about 1 μM-5 μM DMH-1, between about 1 μM-5

µM SB431542, between about 0.2 µM-2 µM purmorphamine, and between about 0.1 µM-1.0 µM RA.

Cells cultured and differentiated according to a method provided herein can be identified as motor neuron progenitors on the basis of OLIG2$^+$ expression. The bHLH transcription factor OLIG2 serves as a unique marker of MN progenitors. The transcriptional repressor function of OLIG2 is both necessary and sufficient to stimulate the expression of a number of downstream homeodomain transcription factors that provide MNs with their unique character. See Briscoe and Novitch, *Philos. Trans. R. Soc. Lond. B. Biol. Sci.* 363(1489):57-70 (2008); see also Shirasaki and Pfaff, *Annu. Rev. Neurosci.* 25:251-281 (2002).

In some cases, a method provided herein further includes a step of culturing OLIG2$^+$ motor neuron progenitors in a MN progenitor differentiation culture medium for approximately one week to generate MNX1$^+$ post-mitotic motor neurons. MNX1 (also known as Motor Neuron and Pancreas Homeobox 1 or HB9) is homeobox gene expressed selectively by motor neurons in the developing vertebrate central nervous system (Arber et al., *Neuron* 23(4):659-74 (1999)). Alternatively, post-mitotic motor neurons can be marked by the expression of ISLET1/2. In some cases, a method provided herein further includes culturing OLIG2$^+$ motor neuron progenitors in a MN progenitor differentiation culture medium for at least about two weeks (e.g., 2 weeks, 2.5 weeks, 3 weeks) to generate choline acetyltransferase-positive (ChAT$^+$) mature motor neurons. Choline acetyltransferase is an enzyme that catalyzes the synthesis of the transmitter acetylcholine for transmitting signals through the neuromuscular junctions and is expressed in somatic, cholinergic (acetylcholine-producing) motor neurons. Mature motor neurons also express VAChAT (vesicular acetylcholine transporter), a neurotransmitter transporter which is essential for storage of acetylcholine (ACh) in secretory organelles and for release of ACh.

In another aspect, the present invention is directed to methods for maintaining a population of motor neuron progenitors. As used herein, the term "maintaining" refers to maintenance of a phenotype (e.g., cell morphology, gene expression profile, differentiation potential) characteristic of a given progenitor for at least 5 weeks, preferably at least 8 weeks, and most preferably at least 10 weeks. For example, the present invention provides methods for maintaining OLIG2$^+$ motor neuron progenitors in vitro for at least 5 weeks.

Methods of maintaining a population of motor neuron progenitors derived from pluripotent stem cells can comprise culturing motor neuron progenitors in a culture medium comprising a Wnt signaling pathway agonist, an inhibitor of the BMP signaling pathway, an inhibitor of the TGFβ signaling pathway, a Notch signaling pathway agonist, a SHE signaling pathway agonist, and a RA signaling pathway agonist. In some cases, such a culture medium is called a maintenance culture medium. Maintaining cells according to a method provided herein can include providing cells with a culture medium comprising an agonist of Notch signaling such as, for example, VPA (Valproic acid). VPA is available from several commercial chemical compound vendors (e.g., Tocris Bioscience, Sigma-Aldrich). VPA is a histone deacetylase (HDAC) inhibitor which can indirectly activate Notch signaling. Stockhausen et al., *Br. J. Cancer.* 92(4):751-759 (2005). Other small molecule inhibitors of HDAC which can be used to activate Notch signaling include, for example, suberoyl bis-hydroxamic acid (SAHA) and sodium butyrate. Accordingly, a culture medium appropriate for use in a method for maintaining motor neuron progenitors can comprise CHIR99021, DMH-1, SB431542, VPA, purmorphamine, and RA.

In an exemplary embodiment, methods for maintaining a population of motor neuron progenitors can comprise culturing motor neuron progenitors in a culture medium comprising between about 1 µM-3 µM CHIR99021; between about 1 µM-5 µM DMH-1; between about 1 µM-5 µM SB431542; between about 0.2 mM-2 mM VPA; between about 0.2 µM-2 µM purmorphamine; and between about 0.1 µM-1.0 µM RA. Under these conditions, motor neuron progenitors maintain long-term OLIG2$^+$ expression without differentiating or switching into other neural progenitor subtypes such as NKX2.2$^+$ V3 interneuron progenitors (p3 domain progenitors). The motor neuron progenitors can be maintained for at least 5 weeks (e.g., at least about 5 passages), yielding previously unobtainable numbers of MN progenitors (producing on the order of 10$^4$ MN progenitors from a single MN progenitor cell).

Methods of Generating and Maintaining Hindbrain Serotonergic Neuron Progenitors

In a further aspect, the present invention is directed to methods for generating and maintaining a population of hindbrain serotonergic neuron progenitors. The terms "serotonergic neuron progenitor" and "serotonergic neural progenitor" are used interchangeably throughout and refer to a progenitor or precursor cell which will mature into a neuron capable of serotonin neurotransmission.

Methods of generating a population of hindbrain serotonergic neuron progenitors can comprise culturing neuroepithelial cells in a culture medium comprising a Wnt signaling pathway agonist, an inhibitor of the BMP signaling pathway, and an inhibitor of the TGFβ signaling pathway plus a SHH signaling pathway agonist for a time sufficient (e.g., about 1 week to about 2 weeks) to induce expression of a hindbrain marker. Hindbrain serotonergic neuron progenitors generated from human pluripotent stem cells according to a method provided herein can be defined based on their expression of hindbrain markers (e.g., GBX2, KROX20, HOXA1-4, HOXB1-4), but not forebrain markers (e.g., FOXG1, OTX2, EMX1, NKX2.1, SIX3), midbrain markers (e.g., EN1, LMX1A, LMX1B, SIM1, LIM1), or spinal cord markers (e.g., HOXB6, HOXB8) besides the neural progenitor markers (e.g., SOX1, SOX2, NESTIN, N-Cadherin, and Ki67).

In an exemplary embodiment, a culture medium for generating a population of hindbrain serotonergic neuron progenitors according to a method provided herein comprises Wnt signaling agonist CHIR99021, BMP signaling inhibitor DMH-1, TGFβ signaling inhibitor SB431542, and SHH signaling pathway agonist purmorphamine. In some cases, the culture medium can comprise between about 1 µM-3 µM CHIR99021; between about 1 µM-5 DMH-1; between about 1 µM-5 µM SB431542; and between about 0.2 µM-2 µM purmorphamine.

Preferably, the method of the present invention does not require cell sorting.

Methods for maintaining a population of hindbrain serotonergic neuron progenitors can comprise culturing hindbrain serotonergic neuron progenitors in a maintenance medium comprising between about 1 µM-3 µM CHIR99021; between about 1 µM-5 µM DMH-1; between about 1 µM-5 µM SB431542; between about 0.2 mM-2 mM VPA, and between about 0.2 µM-2 µM purmorphamine. Under these conditions, serotonergic neuron progenitors maintain long-term NKX2.2$^+$ expression without switching into other neural progenitor subtypes. The serotonergic neural progenitors can be maintained for at least 5 weeks or at least 5 passages.

Methods of Maintaining Other Neuronal Subtype Specific Progenitors

In a further aspect, the present invention is directed to methods for maintaining a population of any other type of neuronal subtype specific progenitors, for example, forebrain GABAergic neuron progenitors, or midbrain dopaminergic neuron progenitors. The phenotype of neuronal subtype specific progenitors is defined by a unique gene expression profile of regional markers and subtype specific markers, and the potential to differentiate into subtype specific mature neurons, For example, forebrain GABAergic neuron progenitor is defined by expression of forebrain markers FOXG1, OTX2B and subtype specific marker NKX2.1, as well as its ability to differentiate into mature neuron secreting GABA neurotransmitter. Similarly, a midbrain dopaminergic neuron progenitor is marked by midbrain transcription factors EN1, EN2 and subtype specific transcription factor LMX1A, as well as its potential to differentiate into mature neuron secreting dopamine neurotransmitter. By "maintaining" a population of progenitors, we mean maintenance of a phenotype for at least 5 passages or at least 5 weeks, preferably at least 8 passages or at least 8 weeks, and most preferably at least 10 passages or at least 10 weeks.

Methods of maintaining a population of neuronal subtype specific progenitors can comprise culturing neuronal subtype specific progenitors in a culture medium comprising a Wnt signaling pathway agonist, an inhibitor of the BMP signaling pathway, an inhibitor of the TGFβ signaling pathway, and a Notch signaling pathway agonist.

The four small molecules, CHIR99021, DMH-1, SB431542, and VPA or their functional equivalents (the core maintaining medium) are required for maintaining the proliferation and phenotype of progenitors. However, other small molecules or patterning factors may be required for maintaining the unique subtype specific progenitors. For example, a SHH signaling pathway agonist and a RA signaling pathway agonist are required in maintaining OLIG2 transcription factor expression in spinal motor neuron progenitors; a SHH signaling pathway agonist is required in maintaining NKX2.2 transcription factor expression in hindbrain serotonergic neuron progenitors.

Improved Method of Generating Pure Motor Neuron Progenitors from Stem Cells

The description of this embodiment of the present invention is based in large part on Example 5 but contains method elements disclosed in the previous embodiments of the present invention, as described above.

Figure 3:
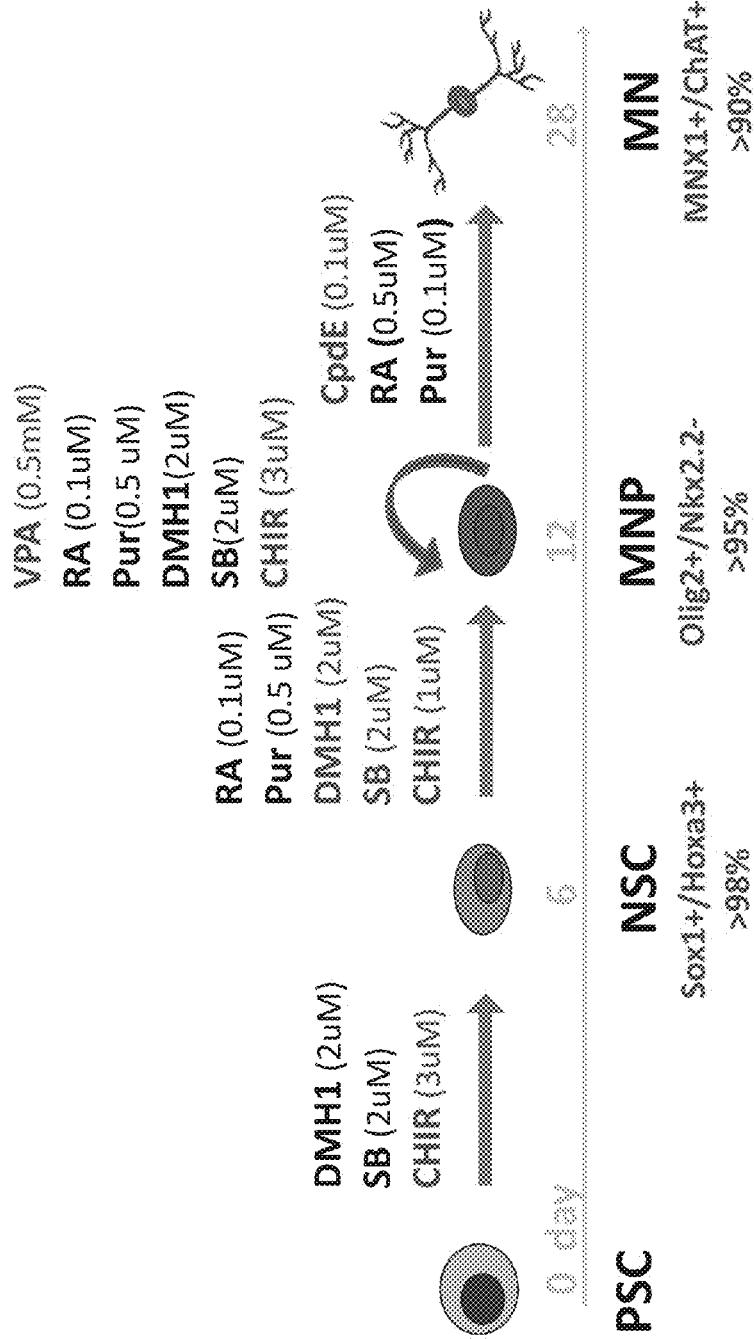
FIG. 3 is a flow chart of an improved method of generating motor neurons. Cmpd E (Compound E, as described below.)

As described above, human pluripotent stem cells (hPSCs) have opened new opportunities for understanding early human development, modeling disease processes and developing new therapeutics. However, some of these applications are hindered by low efficiency and heterogeneity of target cell types differentiated from hPSCs, such as motor neurons (MNs), as well as the inability to maintain the potency of lineage committed progenitors. By using a combination of small molecules that regulate multiple signaling pathways, we have developed a novel method to guide hPSCs to a near-pure population (at least 95%) of OLIG2$^+$ motor neuron progenitors (MNPs) in 12 days and a highly enriched population (at least 90%) of functionally mature MNs in another 16 days. FIG. 3 is a flow chart of our method with preferred reagent concentrations.

More importantly, we have found that the OLIG2$^+$ MNPs can be expanded for at least 5 passages so that a single MNP can be amplified to at least 1×10$^4$. The MNs produced from the expandable MNPs exhibit functional properties, including formation of neuromuscular junctions when co-cultured with skeletal muscle cells and projection of axons toward muscles when grafted into the developing chick spinal cord. The consistent and highly enriched MN populations enable modeling MN degenerative diseases and developing large-scale, MN based screening assays.

The Examples contain specific details of a preferred embodiment. We describe the method in general below:

In general, the present invention is a method of generating populations of motor neuron progenitor (MNP) cells from stem cells, typically first comprising the steps of culturing pluripotent stem cells, as defined above, into neural stem cells (NSCs) in a culture medium comprising a BMP signaling pathway inhibitor, a Wnt signaling pathway agonist, and an inhibitor of activin-nodal signaling.

We describe above typical examples of BMP signaling pathway inhibitors and Wnt signaling pathway agonists. Preferably the BMP signaling pathway inhibitor is selected from the group consisting of DMH-1, Dorsomorphin, and LDN-193189. Most preferably, the inhibitor is DMH1. Typically the Wnt signaling pathway agonist is a GSK3 inhibitor selected from the group consisting of CHIR99021 and 6-bromo-iridium-3'-oxime. Most preferably the agonist is CHIR99021 (CHIR). Preferably, the agonist is used at a concentration of about 3 µM.

The inhibitor of TGFβ signaling is preferably SB431542. (Stemgent). Other suitable inhibitors are described above.

Typically, a population of at least 90%, preferably at least 95%, more preferably at least 98% pure Sox1+/Hoxa3+ neural stem cells is obtained.

One may then culture the neural stem cells in a medium additionally comprising retinoic acid and purmorphamine, as described above. Preferably, the concentration of CHIR is between 1-3 preferably decreased from 3 µM (+/−10%) to 1 µM (+/−10%) relative to the proceeding step, and a population of at least 85%, preferably at least 90%, more preferably at least 95%, pure Olig2+/Nkx2.2− motor neuron progenitor cells is obtained.

In another embodiment, the present invention further comprises the step of culturing the motor neuron progenitor cells in a medium comprising retinoic acid (0.01-1 µM), purmorphamine (0.01-0.5 µM) and a Notch inhibitor, such as compound E (0.05-0.5 µM, Calbiochem), wherein a population, preferably of at least 80%, preferably 85%, more preferably 90% pure, MNX1+/ChAT+ motor neurons is obtained.

Other Notch inhibitors (also known as γ-secretase inhibitors) include DAPT and DBZ.

A preferred timing of cell cultures in the method of the present invention is between 5.5 and 6.5 days for pluripotent stem cells to develop into NSCs and between 5.5 and 6.5 days for NSCs to develop into MNPs. MNPs are preferably cultured for at least 14-17 more days to develop into MN cells.

Of course, one may wish to expand or maintain the MNPs, as described above, before transformation into MNs using the method described above.

In another embodiment, the present invention is a population of Sox1+/Hoxa3+ neural stem cells obtained by the method described above.

In anther embodiment, the present invention is a population of Olig2+/Nkx2.2− motor neuron progenitor cells obtained by the method described above.

In another embodiment, the present invention is a population of MNX1+/ChAT+ motor neuron cells obtained by the method described above. It is a particular advantage of the present invention that this population can be expanded from a single MNP and, thus, particularly useful reagents may be obtained. It is also an advantage that this population exhibits the functional characteristics described above.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Various exemplary embodiments of compositions and methods according to this invention are now described in the following non-limiting Examples. The Examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Efficient Generation of MN Progenitors from hESCs in 2 Weeks

To induce the specification of neuroepithelial cells from human pluripotent cells, the dual TGFβ/BMP inhibition approach was applied for human embryonic stem cells in a monolayer culture. See, for review, Chambers et al., *Nature Biotech.* 27:275-280 (2009). The small molecule SB431542 represses TGFβ signaling by selectively inhibiting Activin receptor-like kinase ALK4/5/7. The small molecule DMH-1 represses BMP signaling by selectively inhibiting the BMP receptor kinase ALK2. Human embryonic stem cells (hESCs) were treated with 2 μM DMH-1 and 2 μM SB431542 for 1 week. Treated hESCs were then induced to differentiate into populations comprising about 85% SOX1+ neuroepithelial cells but also comprising other cell lineages due to spontaneous ESC differentiation, since the dual Nodal/BMP inhibitors SB431542 and DMH-1 are unable to prevent all spontaneous differentiation into other cell lineages, especially when ESC colonies are small. To further improve neural specification, a small molecule that inhibits glycogen synthase kinase-3 (CHIR99021) was applied in combination with DMH-1 and SB431542. GSK3 negatively regulates WNT signaling, and WNT signaling promotes the self-renewal of ESCs and neural progenitors. When exposed to these three molecules for about 6 days, hESCs not only generated more pure populations of SOX1+ neuroepithelial cells (e.g., at least 95% of cells in the total population were SOX1+ neuroepithelial cells), but also generated 2.5-fold more neuroepithelial cells. However, CDS (CHIR99021, DMH-1, and SB431542) treatment-derived neuroepithelial cells showed caudal identity as demonstrated by staining for HOXA2. By contrast, DS (DMH-1 and SB431542) treatment-derived neuroepithelial cells showed rostral identity as demonstrated by staining for OTX2.

The efficiency of motor neuron generation from these two populations of neuroepithelial cells was then compared. After treatment with 0.1 μM Retinoic Acid (RA) and 1 μM purmorphamine (a small molecule for activating SHH signaling) for another 6 days, more than 90% OLIG2+ MN progenitors were induced from CDS treatment-derived neuroepithelial cells, but only 60% from DS treatment-derived neuroepithelial cells. These data suggest an efficient approach for inducing MN progenitors from pluripotent stem cells by contacting the stem cells with a three-molecule cocktail of CDS (CHIR99021, DMH-1, and SB431542) or another cocktail of compounds affecting the Wnt pathway, the BMP pathway, and the TGFβ signaling pathway, respectively, as described herein.

Since the pMN domain is patterned by a gradient of SHH signaling, the efficiency of MN generation upon exposure to different concentrations of purmorphamine was examined. (pMN is a special name in neural development and represents a progenitor domain for motor neuron specification in the spinal cord.) It was observed that 0.5 μM purmorphamine induced a similarly pure population of OLIG2+ MN progenitors as 1 μM (approximately 90% OLIG2+ MN progenitors), but induced few NKX2.2+ p3 progenitors (V3 interneuron progenitors). Concentrations of less than 0.5 μM purmorphamine induced the fewest number of OLIG2+ MN progenitors.

Example 2

Long-term Expansion of OLIG2+ MN Progenitors

Next, we examined whether OLIG2+ MN precursors could be maintained as a continuously dividing population. OLIG2+ MN precursors obtained from the 2-week differentiation were split and cultured under CDS conditions (i.e., in the presence of the 3-molecule CDS cocktail) plus 0.1 μM RA and 0.5 μM purmorphamine. However, the cells gradually lost their dividing potential and became post-mitotic MNs as determined by staining for MNX1, which suggested that RA induces the exit of cell cycle and promotes neurogenesis. Withdrawing RA from the culture was attempted. In the presence of the CDS cocktail plus 0.5 μM purmorphamine, the cells expanded but the neural precursors gradually lost OLIG2 expression and increased NKX2.2 expression, which suggested that purmorphamine alone cannot maintain MN precursors. Instead, the cells switch into p3 domain precursors. Next, motor neuron progenitors were cultured with the CDS cocktail plus RA, purmorphamine, and plus 0.5 mM VPA. VPA can activate Notch signaling pathway, which blocks the neurogenesis induced by RA. This condition can maintain a substantially pure population of OLIG2+ MN progenitors without inducing MNX1+ MNs (e.g., a population substantially devoid of MNX1+ motor neurons) and switch into p3 domain precursors.

Among the four small molecules of the "maintaining" culture medium, CHIR99021 was the core factor for the expansion of MN progenitors since withdrawal of CHIR99021 resulted in a significant loss of dividing potential. DMH-1 and SB431542 cooperated with CHIR99021 to obtain the maximal proliferation. VPA repressed the neurogenesis by blocking the expression of neurogenic transcription factors Ngn2 and Ngn1. RA and purmorphamine are required to maintain the expression of MN progenitor marker OLIG2, which means maintaining the identity and differentiation potential of MN progenitors. Under these conditions, OLIG2+ MN progenitors can be maintained and expanded in culture for at least 5 weeks (e.g., at least 5 passages), yielding previously unobtainable numbers of MN progenitors (on the order of producing $10^4$ MN progenitors from a single MN progenitor cell). It was also observed that OLIG2⁺ MN precursors can be frozen in liquid nitrogen. When thawed and cultured in MN differentiation medium, OLIG2⁺ MN progenitors differentiated into MNX1⁺ post-mitotic motor neurons in 1 week and further into CHAT⁺ mature motor neurons in 2-3 weeks.

Example 3

Differentiating and Maintaining Hindbrain Serotonergic Neural Progenitors

Human embryonic stem cells or induced pluripotent stem cells were seeded onto laminin-coated plates and cultured in human ESC medium for 1 day. (See below for medium components.) On the following day, the culture medium was changed to Neurobasal culture medium comprising 2 µM SB431542, 2 µM DMH1, and 1.0-3.0 µM CHIR99021 for one week. Neural progenitors having hindbrain identity were generated from human pluripotent stem cells. The hindbrain neural progenitors were defined by their expression of hindbrain makers (e.g., GBX2, KROX20, HOXA1-4, HOXB1-4), but not forebrain markers (e.g., FOXG1, OTX2, EMX1, NKX2.1, SIX3), midbrain markers (e.g., EN1, LMX1A, LMX1B, SIM1, LIM1), or spinal cord markers (e.g., HOXB6, HOXB8). The progenitors also included the neural progenitor markers (e.g., SOX1, SOX2, NESTIN, N-Cadherin, and Ki67).

To differentiate neural progenitors toward the serotonergic neural cell fate, hindbrain neural progenitors were cultured in a medium comprising 1000 ng/mL C25II Sonic Hedgehog (SHH) or 1 µM purmorphamine for one week. The resultant cells became ventral hindbrain progenitors expressing hindbrain makers (e.g., GBX2, KROX20, HOXA1-4, HOXB1-4), but not forebrain markers (e.g., FOXG1, OTX2, EMX1, NKX2.1, SIX3). The resultant cells also expressed ventral hindbrain markers OLIG2, NKX6.1, and NKX2.2. The percentage of NKX2.2⁺ cells was as high as 91% of total cells assessed using a FACS assay. These ventral hindbrain neural progenitors could be maintained in a maintenance culture medium comprising 3.0 µM CHIR99021 and 1000 ng/mL C25II Sonic Hedgehog (SHH) or 1 µM purmorphamine for at least 5 passages. The ventral hindbrain neural progenitors were seeded onto polyornithine-coated coverslips, laminin-coated coverslips, or laminin-coated plates for further differentiation in a neural differentiation medium comprising 2.5 µM DAPT (a γ-secretase inhibitor and indirect inhibitor of Notch, a γ-secretase substrate) to enhance maturation.

Example 4

Materials and Experimental Procedures

Human ESC lines H9 and H1 (WiCell Institute, NIH Code 0062 and 0043, passages 18-35) and human iPSC lines (iSMA13 and iSMA23) were cultured on irradiated mouse embryonic fibroblasts (MEFs) as described in the standard hESC protocol available at wicell.org on the World Wide Web.

Retinoic acid, purmorphamine, and SHH stock solutions for addition to a culture medium described herein can be prepared as described by Hu and Zhang (*Methods Mol. Biol.* 636:123-137, 2010).

Generation of OLIG2⁺ MN Progenitors Using a Monolayer Differentiation Method: After treating with 1 mg/ml Dispase, hPSCs were split 1:6 on irradiated MEFs. On the following day, the culture medium was replaced with neural medium (DMEM/F12, Neurobasal® culture medium (Life Technologies) at 1:1, 1×N2 neural supplement, 1×B27 neural supplement, 1 mM ascorbic acid). 3 µM CHIR99021, 2 µM DMH-1, and 2 µM SB431542 were added in fresh medium. The culture medium was changed daily. Human PSCs maintained under these conditions for 6 days were induced into neuroepithelial cells. When treated with 1 mg/ml Dispase, neuroepithelial cells were split at 1:6 on irradiated MEF with the same medium described above. 0.1 µM RA and 0.5 µM purmorphamine were added in combination with CHIR99021, DMH-1, and SB431542. The medium was changed daily. Neuroepithelial cells maintained under these conditions for 6 days differentiated into OLIG2⁺ MN progenitors. We note that this method worked with and without MEFs.

Generation of OLIG2⁺ MN Progenitors Using a Suspension Differentiation Method: After treating with 1 mg/ml Dispase, hPSCs were lifted and cultured as cell aggregates in suspension in hESC medium (DMEM/F12 medium+20% KnockOut™ Serum Replacement (Gibco) supplement, 1×NMAA, 1×glutamax) for four days. On day 4, the hESC medium was replaced with neural medium (DMEM/F12, Neurobasal® culture medium (Life Technologies) at 1:1, 1×N2 neural supplement, 1×B27 neural supplement, 1 mM ascorbic acid). After culturing for another two days, the cell aggregates were attached on the culture plate. The neural medium was changed every other day. After culturing under these conditions for one week, hPSCs were induced into neuroepithelial cells. After treating with 1 mg/ml Dispase, neuroepithelial cells were lifted again and cultured as neurospheres in suspension. 0.1 µM RA and 0.5 purmorphamine were added in neural medium. The medium was changed every other day. Neuroepithelial cells maintained under these conditions for ten days differentiated into OLIG2⁺ MN progenitors.

Maintenance of OLIG2⁺ MN Progenitors: OLIG2⁺ MN progenitors can be frozen in regular freezing medium (DMEM/F12, 10% fetal bovine serum, 10% DMSO). To passage, MN progenitors were treated with 1 mg/ml Dispase and split 1:6 on irradiated MEFs. CHIR99021, DMH-1, SB431542, VPA, purmorphamine, and RA were added at same concentrations as described above. To induce differentiation into mature MNs, CHIR99021, DMH-1, and SB431542 were withdrawn from the medium, and MN progenitors were cultured in the basic neural medium (DMEM/F12, Neurobasal medium at 1:1, 1×N2 neural supplement, 1×B27 neural supplement, and 1 mM ascorbic acid) plus 0.1 µM RA and 0.1 µM purmorphamine for 1 week to generate MNX1⁺ post-mitotic MNs, and then differentiated into CHAT⁺ mature MNs in another 1-2 weeks.

Example 5

Generation and Expansion of Pure Motor Neuron Progenitors from Human Stem Cells

Summary

Human pluripotent stem cells (hPSCs) have opened new opportunities for understanding early human development, modeling disease processes and developing new therapeutics. However, these applications are hindered by low efficiency and heterogeneity of target cell types differentiated from hPSCs, such as motor neurons (MNs), as well as our inability to maintain the potency of lineage committed progenitors. By using a combination of small molecules that regulate multiple signaling pathways, we developed a novel method to guide hPSCs to a near-pure population (>95%) of OLIG2+ motor neuron progenitors (MNPs) in 12 days, and a highly enriched population (>90%) of functionally mature MNs in another 16 days. More importantly, the OLIG2+ MNPs can be expanded for at least 5 passages so that a single MNP can be amplified to $1 \times 10^4$. The MNs produced from the expandable MNPs exhibit functional properties, including formation of neuromuscular junctions when co-cultured with skeletal muscle cells and projection of axons toward muscles when grafted into the developing chick spinal cord. The consistent and highly enriched MN populations enable modeling MN degenerative diseases and developing large-scale, MN based screening assays.

Introduction

Human pluripotent stem cells (PSCs), including embryonic stem cells (ESCs) and induced pluripotent stem cells (iPSCs), offer a new model system to explore early human development and dissect disease processes, as well as an opportunity to devise therapeutics (Grskovic, M., Javaherian, A., Strulovici, B. & Daley, G. Q. Induced pluripotent stem cells—opportunities for disease modeling and drug discovery. *Nat Rev Drug Discov* Vol. 10, 915-929, 2011; Han, S. S., Williams, L. A. & Eggan, K. C. Constructing and deconstructing stem cell models of neurological disease. *Neuron* Vol. 70, 626-644, 2011; Goldman, S. A., Nedergaard, M. & Windrem, M. S. Glial progenitor cell-based treatment and modeling of neurological disease. *Science* Vol. 338, 491-495, 2012). A critical requirement for achieving these potentials is directed differentiation of hPSCs to target cell types. Substantial progress has been made in guiding hPSCs to major cell lineages, including blood, cardiac, and neural cells (Ma, F. et al. Generation of functional erythrocytes from human embryonic stem cell-derived definitive hematopoiesis. *Proc Natl Acad Sci USA* Vol. 105, 13087-13092, 2008; Kattman, S. J. et al. Stage-specific optimization of activin/nodal and BMP signaling promotes cardiac differentiation of mouse and human pluripotent stem cell lines. *Cell Stem Cell* Vol. 8, 228-240, 2011; Liu, H. & Zhang, S. C. Specification of neuronal and glial subtypes from human pluripotent stem cells. *Cell Mol Life Sci* Vol. 68, 3995-4008, 2011). Nevertheless, generation of pure or highly enriched cells, which are often necessary for biochemical analysis, disease modeling, and clinical application, has not been readily achieved. In particular, it is often necessary to induce hPSCs to functionally specialized subtypes of cells, which are only a tiny fraction of cells in a normal tissue/organ of our body. Such a need poses critical challenges to the stem cell field.

Spinal motor neurons (MNs) are a highly specialized type of neurons that reside in the ventral horns and project axons to muscles to control their movement. Degeneration of MNs is implicated in a number of devastating diseases, including spinal muscular atrophy (SMA), amyotrophic lateral sclerosis (ALS), Charcot-Marie-Tooth (CMT) and poliomyelitis (polio) disease. The above disease iPSCs have been generated from patients and attempts have been made to identify disease-related phenotypes and to dissect out the underlying mechanisms before embarking on drug discovery (Ebert, A. D. et al. Induced pluripotent stem cells from a spinal muscular atrophy patient. *Nature* Vol. 457, 277-280, 2009; Egawa, N. et al. Drug screening for ALS using patient-specific induced pluripotent stem cells. *Sci Transl Med* Vol. 4, 145ra104, 2012; Chen, H. et al. Modeling ALS with iPSCs reveals that mutant SOD1 misregulates neurofilament balance in motor neurons. *Cell Stem Cell* Vol. 14, 796-809, 2014; Kiskinis, E. et al. Pathways disrupted in human ALS motor neurons identified through genetic correction of mutant SOD1. *Cell Stem Cell* Vol. 14, 781-795, 2014). However, these efforts are hindered by our inability to produce pure or highly enriched MNs with consistent quality. A number of protocols have been developed, including neural progenitor induction followed by neural patterning by retinoic acid (RA) and sonic hedgehog (SHH) (Li, X. J. et al. Specification of motoneurons from human embryonic stem cells. *Nat Biotechnol* Vol. 23, 215-221, 2005; Qu, Q. et al. High-efficiency motor neuron differentiation from human pluripotent stem cells and the function of Islet-1. *Nat Commun* Vol. 5, 3449, 2014), neural progenitor induction followed by genetic manipulations using adenovirus-mediated gene delivery (Hester, M. E. et al. Rapid and efficient generation of functional motor neurons from human pluripotent stem cells using gene delivered transcription factor codes. *Mol Ther* Vol. 19, 1905-1912, 2011), and differentiation of MNs with above methods followed by sorting with GFP labeling under MNX1 (also known as HB9) promoter (Amoroso, M. W. et al. Accelerated high-yield generation of limb-innervating motor neurons from human stem cells. *J Neurosci* Vol. 33, 574-586, 2013) These differentiation protocols are tedious, time consuming (1 to 2 months), and are of low efficiencies (30-70%) unless by sorting (90%). Furthermore, PSC-derived neurons in vitro, including MNs, are often immature, making it difficult to reveal disease phenotypes that are manifested in functionally mature cells. Hence, there is a critical need to develop a new method that would enable generation of pure and functionally mature MNs with consistent quality and in a short time.

By using a combination of small molecules in a chemically-defined neural medium, we have guided hPSCs to a near-pure population of OLIG2+ motor neuron progenitors (MNPs) in 12 days, and a highly enriched population of functionally mature MNs (>90%) in another 16 days by the use of a Notch inhibitor. Furthermore, we developed a new method to expand a single MNP to $1 \times 10^4$ MNPs, enabling production of a large quantity ($5 \times 10^5$) of consistent MNs from a single stem cell. (We expand a single MNP to approx. 10,000 fold and a single PSC generates approx. 50 MNPs during the first two steps. Therefore, we generate approx. 10,000 MNs from an MNP and 500,000 MNPs from a PSC.) MNs generated by the novel method display molecular phenotypes of SMA and ALS, and can be readily adapted to screening platforms, as illustrated by our luciferase-based axonal length assay using ALS patient MNs.

Results

1. Generation of Pure MNPs by a Small-molecule Cocktail

Specification of MNPs follows serial and overlapping developmental steps: neural induction as well as caudalization and ventralization of neuroepithelial progenitors (NEPs) (Li, X. J. et al. Specification of motoneurons from human embryonic stem cells. *Nat Biotechnol* Vol. 23, 215-221, 2005; Wichterle, H., Lieberam, I., Porter, J. A. & Jessell, T. M., Directed differentiation of embryonic stem cells into motor neurons. *Cell* Vol. 110, 385-397, 2002). In the presence of small molecules, SB431542 (inhibitor of activin-nodal signaling, 2 μM) and DMH1 (inhibitor of BMP signaling, 2 μM) (Chambers, S. M. et al. Highly efficient neural conversion of human ES and iPS cells by dual inhibition of SMAD signaling. *Nat Biotechnol* Vol. 27, 275-280, 2009; Neely, M. D. et al. DMH1, a highly selective small molecule BMP inhibitor promotes neurogenesis of hiPSCs: comparison of PAX6 and SOX1 expression during neural induction. *ACS Chem Neurosci* Vol. 3, 482-491, 2012), hESCs (line H9) were induced to NEPs, with 77±9% of the total differentiated cells being SOX1+ (FIG. 4A, B). Activation of WNT by a small molecular agonist CHIR99021 has been shown to promote neural induction and potentially also neuroepithelial proliferation (Li, W. et al. Rapid induction and long-term self-renewal of primitive neural precursors from human embryonic stem cells by small molecule inhibitors. *Proc Natl Acad Sci USA* Vol. 108, 8299-8304, 2011; Lu, J. et al. Generation of integration-free and region-specific neural progenitors from primate fibroblasts. *Cell Rep* Vol. 3, 1580-1591, 2013). Under the treatment of 3 μM CHIR together with 2 μM SB+2 μM DMH-1 for 6 days, nearly all the differentiated cells were SOX1$^+$ NEPs (>98%) (FIG. 4A, B). CHIR not only augmented the efficiency of neural induction, but also increased the yield of SOX1$^+$ NEPs by 2.8 fold (FIG. 4B). Wnt activation (by CHIR) often induces a caudal fate of neural progenitors (Xi, J. et al. Specification of midbrain dopamine neurons from primate pluripotent stem cells. *Stem Cells* Vol. 30, 1655-1663, 2012). Indeed, CHIR-induced NEPs showed a caudal identity with HOXA3 expression. In contrast, NEPs induced by SB+DMH1 (without CHIR) exhibited a rostral identity with OTX2 expression (FIG. 4B). Therefore, treatment of CHIR+SB+DMH-1 combines the steps of induction and caudalization of NEPs, representing a chemically-defined, single-step method for obtaining homogenous caudal NEPs from hPSCs.

The next step is to specify OLIG2$^+$ MNPs by mimicking the ventralization of NEPs in vivo. By exposing the CHIR+SB+DMH-1-induced caudal-like NEPs to RA (0.1 μM) and Pur (Purmorphamine, SHH signalling agonist, 1 μM) for 6 days, which was identified in our previous study (Li, X. J. et al. Directed differentiation of ventral spinal progenitors and motor neurons from human embryonic stem cells by small molecules. *Stem Cells* Vol. 26, 886-893, 2008), we obtained 81±9% OLIG2-expressing neural progenitors (FIG. 4C). However, about 40% OLIG2$^+$ cells co-expressed NKX2.2, another ventral spinal cord marker (FIG. 4C). During neural development, OLIG2 and NKX2.2 are initially induced in a common pool of progenitors that ultimately segregate into unique territories giving rise to distinct OLIG2$^+$ MNPs and NKX2.2$^+$ interneuron progenitors (Lee, S. K. & Pfaff, S. L. Transcriptional networks regulating neuronal identity in the developing spinal cord. *Nat Neurosci* Vol. 4 Suppl, 1183-1191, 2001). WNT signalling plays a critical role in this segregation (Wang, H., Lei, Q., Oosterveen, T., Ericson, J. & Matise, M. P. Tcf/Lef repressors differentially regulate Shh-Gli target gene activation thresholds to generate progenitor patterning in the developing CNS. *Development* Vol. 138, 3711-3721, 2011). We thus added WNT agonist CHIR in combination with RA and Pur. Under the treatment of CHIR+RA+Pur for 6 days, NKX2.2 expression was completely repressed in the culture, but OLIG2-expressing population was also decreased to 62±5% (FIG. 4C). We reasoned that WNT signalling may elevate the threshold of SHH signalling necessary to induce OLIG2 expression. However, at the increased concentration, SHH agonist Pur became toxic to the NEPs. We thus took an alternative approach to decrease the threshold of SHH signalling by repressing the dorsalizing molecule of the spinal cord, BMP signalling. Addition of dual SMAD inhibitors SB and DMH-1 in combination with CHIR+RA+Pur significantly increased OLIG2$^+$/NKX2.2$^-$ cell population (FIG. 4C). By serial titration of Pur and CHIR in combination with RA, SB and DMH-1 (FIG. 8), we found that treatment with 1 μM CHIR, 2 μM SB, 2 μM DMH-1, 0.1 μM RA and 0.5 μM Pur for 6 days resulted in a robust population of OLIG2$^+$ MNPs (95±3%), among which few (<0.5%) OLIG2/NKX2.2 double positive cells were found (FIG. 4C).

Our protocol for OLIG2+ MNP specification is highly reproducible in multiple different hPSC lines, including normal iPSC line IMR90, ALS iPSC lines SOD1-D90A and SOD1-A4V, and SMA iPSC lines SMA13 and SMA232. Under the treatment of CHIR+SB+DMH1 for 6 days and CHIR+SB+DMH1+RA+Pur for another 6 days, all the hPSC lines generated more than 90% OLIG2$^+$ MNPs (FIG. 4D). Thus, coordinated specification and patterning of neuroepithelia by small molecules lead to robust generation of pure populations of region-specific MNPs.

2. MNPs are Expanded to Large Numbers.

Developmentally, OLIG2$^+$ MNPs are present transiently and they transition to other neuronal (interneuron) and glial (oligodendrocyte) lineages after generation of MNs. For cellular and biochemical analysis, it is crucial to expand the MNPs without losing their ability to produce MNs, which has not been achieved. Since the CHIR+SB+DMH1+RA+Pur condition is highly efficient in specifying and generating MNPs, we asked if the condition could expand the OLIG2$^+$ MNPs in a continuously dividing state. We first examined whether RA and Pur are required for maintaining OLIG2 expression. The MNPs were passaged weekly under the CHIR+SB+DMH1 condition with or without Pur or RA+Pur. After two passages, OLIG2$^+$ MNPs were decreased to 35±5% in the control group (without Pur and RA), to 62±5% in Pur group, and a large population of NKX2.2$^+$ cells appeared in these two groups. In the RA+Pur group, OLIG2$^+$ MNPs were maintained at 91±3% with rare NKX2.2$^+$ cells (FIG. 5A). Therefore, RA and Pur are required for maintaining the identity of MNPs.

We then examined whether CHIR, SB and DMH-1 are required for maintaining cell proliferation. The MNPs were passaged under the RA+Pur condition and divided into three groups: SB+DMH-1 treatment group, CHIR treatment group, and CHIR+SB+DMH-1 treatment group. After two passages, the cell population expressing Ki-67, a cell proliferation marker, was at less than 8%, 81±6%, and 92±4% in the SB+DMH-1 group, the CHIR group, and the CHIR+SB+DMH-1 group, respectively (FIG. 5B). Therefore, CHIR+SB+DMH-1 are required for maintaining the proliferation of MNPs at the maximum level.

When the MNPs were expanded in the same medium (CHIR+SB+DMH-1+RA+Pur) for longer than two passages, the OLIG2-expressing MNP population decreased with a concomitant appearance of MNX1 expressing MNs, suggesting that some MNPs have exited cell cycle and differentiated to neurons. We reasoned that this is likely due to the neurogenic effect of RA. It was known that valproic acid (VPA), a histone deacetylase inhibitor, can repress neurogenesis by indirectly activating Notch signalling (Stockhausen, M. T., Sjölund, J., Manetopoulos, C. & Axelson, H. Effects of the histone deacetylase inhibitor valproic acid on Notch signalling in human neuroblastoma cells. *Br J Cancer* Vol. 92, 751-759, 2005). We thus added VPA to the culture system. Under this culture condition, the MNPs were expanded for at least 5 passages yet maintained OLIG2 expression at 82±9% (FIG. 5D). Further culturing under this condition resulted in gradual decrease of OLIG2$^+$ cell population and increase of NKX2.2$^+$ cell population, suggesting a need of an alternative strategy for an even longer term expansion. Nevertheless, continual expansion of MNPs for 5 passages allows amplification of a single MNP to 1×10$^4$ MNPs, translating to the generation of >5×10$^5$ MNPs from a single hPSC (FIG. 5E). Furthermore, these MNPs can be frozen and thawed in regular conditions with over 90% recovery.

3. MNPs Differentiate into Enriched Functional MNs.

To determine the differentiation of expanded MNPs, we withdrew CHIR+SB+DMH-1, increased RA concentration (0.5 μM), and reduced Pur (0.1 μM). After 6 days, nearly all the MNPs differentiated into MNs, as evidenced by expression of MNX1 (90±9%) or ISL1 (95±3%) (FIG. 6A, B). Further culture on MATRIGEL or astrocyte feeders for two weeks resulted in generation of more mature MNs that expressed CHAT, although the CHAT$^+$ MN population (47±9%) was substantially lower than the MNX1$^+$ MNPs. We reasoned that the lower population of CHAT$^+$ mature MNs may be due to proliferation of the small number of neural precursors and their subsequent differentiation to other neuronal types via lateral inhibition of NOTCH signaling (Lewis, J., Notch signalling and the control of cell fate choices in vertebrates. *Semin Cell Dev Biol* Vol. 9, 583-589, 1998). To overcome this inefficiency of MN maturation, we applied Compound E (Cpd E), a NOTCH signaling inhibitor in the MN culture. CpdE treatment resulted in a near homogenous MAP2$^+$ mature neuronal cultures without any proliferating cells (Ki67$^+$), and about 91±6% of MAP2$^+$ neurons expressed CHAT (FIG. 6A, B). These CHAT+MNs were electrophysiologically active, as defined by their ability to elicit action potentials in response to depolarizing current injection in current-clamp recordings (FIG. 9). Therefore, CpdE not only increases the mature MN population but also substantially shortens the maturation process.

To determine whether the CpdE-accelerated MNs are functional, we co-cultured the MNs with differentiated myotubes from mouse C2C12 cells. After 10 days of co-culture, we observed aggregated BTX$^+$ acetylcholine receptors on myotubes and their overlapping with CHAT$^+$ neurites (FIG. 6C), suggesting formation of neuromuscular junctions. To study the ability of motor neurons to project axons toward the muscle targets, CpdE treated MNs were transplanted in ovo into the lesioned neural tube of chicken embryos at HH stage 15-16. Transplanted embryos showed successful engraftment of human MNs (as marked by GFP expression) into the ventral horn (FIG. 6D). Importantly, we observed GFP labelled human MN axons (CHAT$^+$) projected ventrally through the ventral roots and along the peripheral nerves of the host (FIG. 6D'). These data indicate that mature MNs generated by CpdE treatment exhibit proper functions.

4. Enriched MNs Enable Presentation of Disease Phenotypes and Building of Screening Platforms.

Most neurodegenerative diseases, like SMA and ALS, preferentially affect one type of neurons such as MNs. Genetically linked disorders, including SMA and ALS, may lead to changes in gene dosage of less than 50%. Hence, it will be technically difficult to discern changes in gene expression if the population of disease target cells is not highly enriched. To determine the utility of the MNs generated with the above method, we measured the expression of genes that are known to be altered in SMA and ALS. In this analysis, we generated spinal non-MNs from the same iPSCs as a control by replacing Pur with Cyclopamine (Cyc) to block SHH signaling (FIG. 10A). Under RA and Cyc treatment for 6 days, the induced spinal neural precursors were void of OLIG2 expression, and the differentiated neurons were void of MNX1 and CHAT expression, but with GABA expression (FIG. 10B, C). Using these highly enriched MNs and GABA neurons, we found that the mRNA of survival motor neuron (SMN, the protein affected in SMA) was decreased in both MNs and GABA neurons that were derived from SMA patients as compared to those from non-SMA iPSCs (FIG. 7A). This is consistent with the fact that SMN mutations affect all cell types. Interestingly, we found that MNs exhibited even lower (38±4%) SMN than GABA neurons (60±6%) (FIG. 7A), again consistent with a previous report that MNs express markedly lower levels of full-length SMN transcripts from SMN2 gene than do other cells in the spinal cord (Ruggiu, M. et al. A role for SMN exon 7 splicing in the selective vulnerability of motor neurons in spinal muscular atrophy. *Mol Cell Biol* 32, 126-138, 2012). Similarly in ALS caused by mutations in superoxide dismutase (SOD1) gene, MNs display neurofilament (NF) aggregation that is attributed to the decreased level of light polypeptide neurofilament (NEFL) (Chen, H. et al. Modeling ALS with iPSCs reveals that mutant SOD1 misregulates neurofilament balance in motor neurons. *Cell Stem Cell* 14, 796-809, 2014). We found a 45±4% reduction of NEFL mRNA in D90A MNs, but not GABA neurons, when compared to genetically corrected (D90D) MNs and GABA neurons (FIG. 7B). Together, these data indicate that the enriched MNs generated from patient iPSCs using our new method enable identification of disease related phenotypes.

Figure 11:
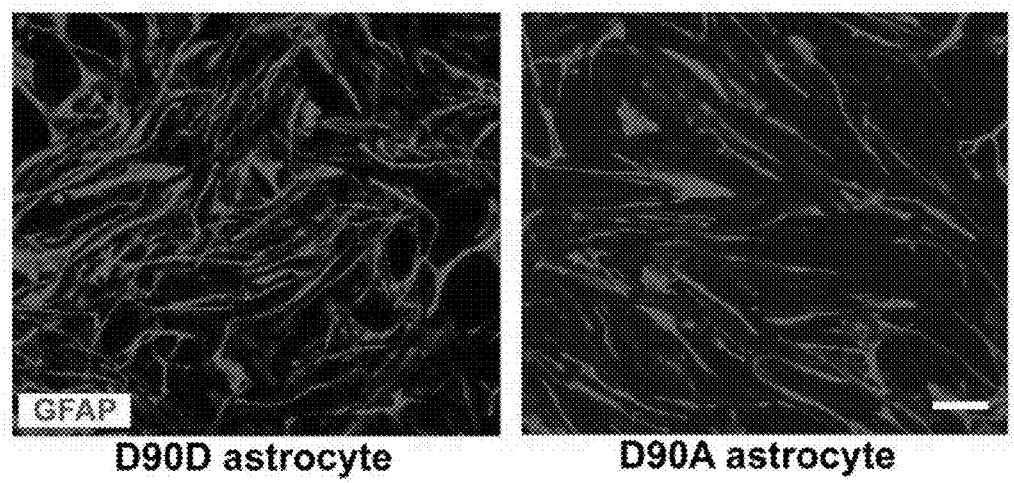
FIG. 11 shows the ALS mutant and corrected astrocytes. Immunofluorescent images of ALS mutant (D90A) and corrected (D90D) astrocytes differentiated from hiPSCs for 6 months. Scale bars: 50 µm.

Our ability to generate large quantities of consistent MNs offers an opportunity for building high-throughput screening platforms for MN diseases. In ALS, astrocytes enhance disease progression by promoting axonal degeneration and MN death (Di Giorgio, F. P., Carrasco, M. A., Siao, M. C., Maniatis, T. & Eggan, K. Non-cell autonomous effect of glia on motor neurons in an embryonic stem cell-based ALS model. *Nat Neurosci* Vol. 10, 608-614, 2007; Nagai, M. et al. Astrocytes expressing ALS-linked mutated SOD1 release factors selectively toxic to motor neurons. *Nat Neurosci* Vol. 10, 615-622, 2007; Haidet-Phillips, A. M. et al. Astrocytes from familial and sporadic ALS patients are toxic to motor neurons. *Nat Biotechnol* Vol. 29, 824-828, 2011). Indeed, when ALS iPSC-derived MNs were grown on top of ALS (D90A SOD1) or genetically corrected (D90D SOD1) astrocytes (FIG. 11) in a medium that lacks neurotrophic factors, MNs began to show neurite fragmentation with reduced neurite length on D90A but not D90D astrocytes at Day 10 (FIG. 7C). To enable automated measurement of neurite length for high throughput screening, we established a reporter iPSC line (from D90A SOD1) with a luciferase reporter NanoLuc (Nluc) fused with SYNAPTOPHYSIN (SYP) (FIG. 7D), a synaptic vesicle glycoprotein, which targets the Nluc reporter to axonal membrane, not cytoplasm (Nakata, T., Terada, S. & Hirokawa, N. Visualization of the dynamics of synaptic vesicle and plasma membrane proteins in living axons. *J Cell Biol* Vol. 140, 659-674, 1998). We first established the linear relationship between Nluc expression and MN numbers by measuring luciferase activity of cultures 10 days after plating different numbers of SYP-Nluc expressing MNs (1250, 2500, 5000, 10000 and 20000 cells) on astrocytes (FIG. 12A). We then tested whether the Nluc reporter activity is correlated with the reduced axonal length. Same numbers of SYP-Nluc expressing MNs were plated on D90D and D90A astrocytes and the Nluc activity was detected at Day 10. The Nluc activity on D90A astrocytes was significantly decreased to 70.5±2.7%, comparing to the D90D astrocyte group (FIG. 12B). Next, we exposed the co-cultures to three compounds, Riluzole (Rilu) (Miller, R. G., Mitchell, J. D. & Moore, D. H. Riluzole for amyotrophic lateral sclerosis (ALS)/motor neuron disease (MND). *Cochrane Database Syst Rev* Vol. 3, CD001447, 2012), the only approved drug for ALS, as well as Kenpaullone (Ken) and EphA inhibitor (EphAi) that are known to rescue axonal degeneration in ALS cell models (Yang, Y. M. et al. A small molecule screen in stem-cell-derived motor neurons identifies a kinase inhibitor as a candidate therapeutic for ALS. *Cell Stem Cell* Vol. 12, 713-726, 2013; Van Hoecke, A. et al. EPHA4 is a disease modifier of amyotrophic lateral sclerosis in animal models and in humans. *Nat Med* Vol. 18, 1418-1422, 2012). Riluzole had no effect on Nluc activity. Ken and EphAi increased the Nluc activity to 1.5 and 2.8 fold in both D90A and D90D groups (FIG. 7E), indicating that they increased axonal length. However, Ken and EphAi did not specifically rescue the axonal length of MNs induced by ALS astrocytes, as the ratio of Nluc activity on D90A astrocytes versus D90D astrocytes remained at 70% (FIG. 7E). These results provide a proof of principle for the use of our enriched, patient-derived MNs for drug screening and suggest its potential for identifying disease specific targets.

Discussion

We have developed a novel strategy for guiding hPSCs to a near-pure population of OLIG2$^+$ MNPs in 12 days by coordinating signaling pathways using small molecules, and subsequently a highly enriched population of functionally mature MNs (>90%) in another 16 days by the use of a Notch inhibitor.

Furthermore, we have devised a method to expand a single MNP to 1×10$^4$ MNPs, enabling production of a large quantity (5×10$^5$) of consistent MNs from a single stem cell. Our novel method enables presentation of disease phenotypes and building of screening platforms, as illustrated by our luciferase-based axonal length assay using ALS patient MNs.

Compared to previous methods, our method has at least two critical improvements. The first is the application of WNT agonist during MNP differentiation. WNT signaling is a more efficient pathway to caudalize neural progenitors (Xi, J. et al. Specification of midbrain dopamine neurons from primate pluripotent stem cells. *Stem Cells* Vol. 30, 1655-1663, 2012). Thus, the combination of WNT activator (CHIR99021) with BMP inhibitor (DMH1) and TGFb inhibitor (SB431542) induced homogenous caudal NEPs from hPSCs. Most importantly, WNT signaling plays a critical role in MNP specification. All previous methods used RA and SHH to induce OLIG2$^+$ MNPs without examining other ventral spinal markers, especially co-expression of NKX2.2. We showed here that use of RA and SHH generated mixed ventral progenitors with a large population of cells that co-express OLIG2 and NKX2.2. During spinal cord development, OLIG2 and NKX2.2 are initially induced in a common pool of progenitors that ultimately segregate into unique territories, giving rise to distinct OLIG2$^+$ MNPs (pMN domain) and NKX2.2$^+$ interneuron progenitors (p3 domain) (Lee, S. K. & Pfaff, S. L. Transcriptional networks regulating neuronal identity in the developing spinal cord. *Nat Neurosci* Vol. 4 Suppl, 1183-1191, 2001). Without segregation, NKX2.2 could interfere with the differentiation of OLIG2$^+$ progenitors to MNX1$^+$ MNs, which is one of the reasons why some previous methods induced a high percentage of OLIG2$^+$ progenitors, but ended with a small population of MNX1$^+$ MNs. WNT signaling was reported to selectively oppose SHH-mediated induction of NKX2.2, but have little effect on OLIG2, and thereby establish their distinct expression domains in cooperation with graded SHH signaling (Wang, H., Lei, Q., Oosterveen, T., Ericson, J. & Matise, M. P. Tcf/Lef repressors differentially regulate Shh-Gli target gene activation thresholds to generate progenitor patterning in the developing CNS. *Development* Vol. 138, 3711-3721, 2011). As WNT elevates the strength of SHH signaling to induce OLIG2 expression, the two inhibitors of dorsalizing BMP signaling (Dorsomorphin and LDN-193189) were also included. Therefore, our method of combining small molecules regulating WNT, SHH, RA and BMP signals closely mimics the cooperation of these signals in the spinal cord development in vivo to specify the region-specific OLIG2$^+$ MNPs.

The second improvement is the application of a NOTCH inhibitor during MN maturation. Lateral inhibition mediated by NOTCH signaling is an intrinsic mechanism to guide orderly transition of mitotically active precursors into different types of post-mitotic neurons and glia at different stages (Lewis, J. Notch signaling and the control of cell fate choices in vertebrates. *Semin Cell Dev Biol* Vol. 9, 583-589, 1998). The treatment with NOTCH inhibitor CpdE in our method synchronizes the differentiation of OLIG2$^+$ MNPs to generate homogenous mature MNs without mixing with any other neural cells. With these two improvements, our method robustly generates almost homogenous mature MNs, which exhibit functional properties, including formation of neuromuscular junctions when co-cultured with skeletal muscle cells and projection of axons toward muscles when grafted into the developing chick spinal cord. More significantly, the MNs derived from disease iPSCs by our method exhibit the MN-specific molecular phenotypes, including down-regulation of full-length SMN in SMA and down-regulation of NEFL level in ALS, which would be nearly impossible to detect with previous methods that only generate a small population of MNs in the mixed culture.

A large quantity of consistent target cells, such as mature MNs, is necessary for high-throughput screening. In general, lineage committed progenitors can be expanded, but quickly lose their differentiation potency. For example, OLIG2$^+$ MNPs can be expanded with FGF and/or EGF, but quickly lose the potency of MN differentiation in two passages. Several recent reports described the expansion of neural progenitors with small molecules of WNT and/or SHH signaling (Li, W. et al. Rapid induction and long-term self-renewal of primitive neural precursors from human embryonic stem cells by small molecule inhibitors. *Proc Natl Acad Sci USA* Vol. 108, 8299-8304, 2011; Reinhardt, P. et al. Derivation and expansion using only small molecules of human neural progenitors for neurodegenerative disease modeling. *PLoS One* Vol. 8, e59252, 2013). However, as shown in this study (FIG. 5A), their ability to maintain MN potential is still significantly diminished during cell passages compared to our method. Our method can expand MNPs for at least 5 passages to amplify a single MNP to 1×10$^4$ MNPs, or generate 5×10$^5$ MNs from single hPSC. This provides a sufficient cell source for high-throughput drug screening, as shown in our screening platform for MN axonal degeneration. In summary, our new method enables generation of large quantities of MNs with consistency and high purity, providing a basis for modeling MN diseases in vitro and for drug discovery.

Methods

Human Pluripotent Stem Cells (PSCs).

The human PSC lines used in this study are listed in Table 1. Fibroblasts from a 50-y-old female ALS patient carrying the D90A SOD1 mutation (ND29149, Coriell Institute, coriell.org), a 3-y-old male SMA patient (GM03813, Coriell Institute) and a 7-m-old SMA patient (GM00232, Coriell Institute) were reprogrammed using the non-integrating Sendai virus as described (Ban et al., 2011) to established iPSC lines ALS-D90A, SMA13 and SMA232. D90D iPSC line was established by correcting the D90A SOD1 mutation in ALS-D90A lines by TALEN technology (Chen et al., 2014). A4V SOD1 mutant ALS iPSC line, established with retrovirus, was obtained from Coriell (ND35671). Human ESC line H9 (WA09 line, NIH registry 0046) and normal iPSC line IMR90-4 were obtained from WiCell. All the PSCs were cultured on irradiated mouse embryonic fibroblasts (MEFs) as described in the standard protocol http://www.wicell.org.

MNP Specification and MN Differentiation.

To generate MNPs, hPSCs were dissociated with Dispase (1 mg/ml) and split 1:6 on irradiated MEFs or MATRIGEL™ coated plates. On the following day, the PSC medium was replaced with a chemically defined neural medium, including DMEM/F12, Neurobasal medium at 1:1, 0.5×N2, 0.5×B27, 0.1 mM ascorbic acid (Santa Cruz), 1×Glutamax and 1×penicillin/streptomycin (All other reagents, such as culture medium minus absorbic acid, from Invitrogen). CHIR99021 (3 uM, Torcris), 2 µM DMH-1 (Tocris) and 2 µM SB431542 (Stemgent) were added in the medium. The culture medium was changed every other day. Human PSCs maintained under this condition for 6 days were induced into NEP cells. The NEP cells were then dissociated with Dispase (1 mg/ml) and split at 1:6 with the same medium described above. RA (0.1 µM, Stemgent) and 0.5 µM Purmorphamine (Stemgent) were added in combination with 1 µM CHIR99021, 2 µM DMH-1 and 2 µM SB431542. The medium was changed every other day. NEP cells maintained under this condition for 6 days differentiated into OLIG2+ MNPs. The OLIG2+ MNPs were expanded with the same medium containing 3 µM CHIR99021, 2 µM DMH-1, 2 µM SB431542, 0.1 µM RA, 0.5 µM Purmorphamine and 0.5 mM VPA (Stemgent), and split 1:6 to 1:8 once a week with Dispase (1 mg/ml). OLIG2+ MNPs were frozen with the regular freezing medium (DMEM/F12, 10% fetal bovine serum and 10% DMSO) in liquid nitrogen, and cultured again in expansion medium after thawing.

To induce MN differentiation, OLIG2+ MNPs were dissociated with Dispase (1 mg/ml) and cultured in suspension in the above neural medium with 0.5 µM RA and 0.1 µM Purmorphamine. The medium was changed every other day. OLIG2+ MNPs under this condition for 6 days differentiated into MNX1+ MNs. The MNX1+ MNs were then dissociated with Accumax™ (eBioscience) into single cells and plated on MATRIGEL™ coated plates or on astrocytes. The MNX1+ MNs were cultured with 0.5 µM RA, 0.1 µM Purmorphamine and 0.1 µM Compound E (Calbiochem) for 10 days to mature into CHAT+ MNs. Insulin-like growth factor 1 (IGF-1), brain-derived neurotrophic factor (BDNF), and ciliary neurotrophic factor (CNTF) (all from R&D, 10 ng/ml each) were added if MNs were plated at low density (for example, at about 10,000 cells per cm$^2$ the MNs grow as a single neuron, not a cluster). For identifying MN disease phenotypes, SMA and ALS MNs were cultured without these factors.

Functional Analysis of Mature MNs.

Whole-cell patch-clamp recordings were performed on iPSC-derived CHAT+ neurons at Day 28 after iPSC differentiation as we described (Chen, H. et al. Modeling ALS with iPSCs reveals that mutant SOD1 mis-regulates neurofilament balance in motor neurons. *Cell Stem Cell* Vol. 14, 796-809, 2014).

To examine neuromuscular junction formation, C2C12 cells were seeded on MATRIGEL coated plate in DMEM with 10% FBS, and then were induced to form myotube by switching to DMEM containing 2% FBS. Day 18 MNX1+ MNs derived from hPSCs were plated onto myotubes and cultured in maturation condition for 7 days, after which the neuromuscular synapses were visualized using CHAT and BTX staining.

To perform transplantations, Day-18 MNX1+ MN spheres were triturated with a 1-ml pipette tip 5-7 times and treated with CpdE for 24 hrs. (We mostly culture the cells as adherent cultures in our methods. In a transplantation application we use spheres because the detached and dissociated MNs don't survive well in transplantation.) Transplantation was performed as previously described (Wichterle, H., Lieberam, I., Porter, J. A. & Jessell, T. M. Directed differentiation of embryonic stem cells into motor neurons. *Cell* Vol. 110, 385-397, 2002). Briefly, after a small suction lesion at the prospective intraspinal site was created in a chick embryo at stage 15-18 at somites 15-20, MN spheres were loaded into a handheld micro-injector and placed into the lesion. After 6 days, the chicks were sacrificed, fixed with 4% PFA for 2 h at 4° C., and neurite outgrowth was accessed by cutting 30 µm sections of the spinal cord near the injected site.

qPCR Analysis

Total RNAs were isolated with RNeasy Plus Mini Kit (Qiagen) according to the manufacturer's instructions. For qPCR, cDNA was synthesized from 1 ug total RNAs using iScript™ reverse transcription supermix (Biorad). qPCR was performed using iTaq™ Universal SYBR® Green Supermix (Biorad). Sequences of the primers are shown in Table 2. GAPDH gene was used as internal control to equalize cDNA.

Immunostaining and Microscopy

Immunohistochemical staining was performed according to Zhang et al (2001). The following primary antibodies were used: SOX1 (gIgG 1:1000, R&D), OTX2 (mIgG, 1:2000, DSHB), HOXA3 (mIgG 1:1000, R&D), OLIG2 (rIgG 1:500, Chemicon), NKX2.2 (mIgG 1:100, DSHB), Ki67 (rIgG 1:200, Chemicon), MNX1 (mIgG 1:50, DSHB), ISL1 (mIgG 1:1000, DSHB), TUJ1 (rIgG 1:5000, Covance), CHAT (gIgG 1:300, Chemicon), MAP2 (mIgG 1:1000, Chemicon), GABA (mIgG 1:1000, Chemicon), FoxP1 (rIgG, 1:1000, Chemicon).

MN-astrocyte Co-culture and Luciferase Assay

The luciferase reporter NanoLuc (Nluc) was obtained from Promega. The SYP-Nluc reporter iPSC line was established by inserting SYP-Nluc fusion reporter in the AAVS1 site by the TALEN technology (Qian et. al, 2014). Astrocytes were differentiated from the isogenic iPSC lines D90D and D90A for 6 months by the protocol established in our lab (Krencik et. al, 2011). The astrocytes were plated at 1×10$^4$ cells/well in white 96-well plates (Greiner Bio-one) and cultured in the astrocyte medium (DMEM, 10% FBS) for 7 days. The D90A MNX1+ MNs derived from SYP-Nluc reporter iPSC line were then plated at 1×10$^4$ cells/well on astrocytes and cultured in a nutrition deficient medium (DMEM/F12, Neurobasal medium at 1:1, 1×N2, 0.5 µM RA, 0.1 µM Purmorphamine and 0.1 µM Compound E). For testing the compounds, Riluzole (50 µM, Torcris), Kenpaullone (5 µM, Tocris) and EphA inhibitor (50 µM, Calbiochem) were added in the medium. After coculturing for 10 days, the Nluc activity was detected by Nano-Glo® Luciferase Assay (Promega) according to the manufacturer's instructions.

Statistical Analyses

For quantifications, experiments were performed at least in triplicates. Statistical significance was assessed using one-way ANOVA followed by Tukey's test. Data were presented as mean±SEM.

TABLE 1

Human pluripotent stem cell lines used in this study

| Cell line | Diagnosis | Gender | Age | ESC/iPSC |
|---|---|---|---|---|
| H9 | normal | female | blastocyst | ESC |
| IMR90 | normal | female | fetal | iPSC |
| D90A | ALS (SOD1 mutation) | female | 50 | iPSC |
| A4V | ALS (SOD1 mutation) | female | 65 | iPSC |
| SMA13 | SMA | male | 3 | iPSC |
| SMA232 | SMA | male | 0.6 | iPSC |

TABLE 2

Primers used in qPCR analysis

| Primer name | sequence |
|---|---|
| SMN full length forward | CACCACCTCCCATATGTCCAGATT (SEQ ID NO: 1) |
| SMN full length reverse | GAATGTGAGCACCTTCCTTCTTT (SEQ ID NO: 2) |
| SMN total forward | ATGAGCTGTGAGAAGGGTGTTG (SEQ ID NO: 3) |
| SMN total reverse | TTGCCACATACGCCTCACATAC (SEQ ID NO: 4) |
| NEFL forward | TTTCACTCTTTGTGGTCCTCA (SEQ ID NO: 5) |
| NEFL reverse | AGACCCTGGAAATCGAAGC (SEQ ID NO: 6) |
| GAPDH forward | CTCTCTGCTCCTCCTGTTCGAC (SEQ ID NO: 7) |
| GAPDH reverse | TGAGCGATGTGGCTCGGCT (SEQ ID NO: 8) |

---

We claim:

1. A method of generating populations of motor neuron progenitor cells from neural stem cells, comprising the steps of
   (a) culturing neural stem cells in a culture medium comprising:
      a Wnt signaling pathway agonist, wherein the Wnt signaling pathway agonist is a GSK3 inhibitor selected from the group consisting of CHIR99021 and 6-bromo-iridium-3'-oxime, and wherein the Wnt signaling pathway agonist is used at a concentration of about 1 μM to 3 μM,
      a bone morphogenetic protein (BMP) signaling pathway inhibitor selected from the group consisting of DMH-1, Dorsomorphin, and LDN-193189, wherein the concentration of the BMP signaling pathway inhibitor is about 1 μM to 5 μM,
      an inhibitor of activin-nodal signaling, wherein the inhibitor of activin-nodal signaling is SB431542 in an amount of about 1 μM to 5 μM,
      retinoic acid in an amount of about 0.1 μM to 1 μM, and
      purmorphamine in an amount of about 0.1 μM to about 1 μM,
   (b) detecting within the cultured cells of step (a) a population positive for Olig2 and negative for Nkx2.2, wherein a population of at least 85% pure Olig2±/Nkx2.2− motor neuron progenitor cells is obtained.

2. The method of claim 1, further comprising the step of
   (c) culturing the Olig2+/Nkx2.2− motor neuron progenitor cells in a medium comprising retinoic acid, purmorphamine and a Notch signaling inhibitor, wherein the Notch inhibitor is selected from the group consisting of (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide (compound E), N-[(3,5-Difluorophenyl)acetyl]-L-alanyl-2-phenyl] glycine-1,1-dimethylethyl ester (DAPT), and Dibenzazepine (DBZ),
   (b) detecting MNX1 and ChAT markers on the cells cultured in step (c), wherein a population of at least 80% pure MNX1+/ChAT+motor neurons is obtained.

3. The method of claim 1, wherein the Wnt signaling pathway agonist is CHIR99021.

4. The method of claim 1, wherein the concentration of the Wnt signaling pathway agonist is about 1 μM.

5. The method of claim 2, wherein the Notch signaling pathway inhibitor is (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide (compound E).

6. The method of claim 2, wherein the culture medium comprises 0.01 µM-1 µM retinoic acid, 0.01 µM-0.5 µM purmorphamine, and 0.05 µM-0.5 µM compound E.

* * * * *

UNITED STATES PATENT AND TRADEMARK OFFICE
CERTIFICATE OF CORRECTION

PATENT NO. : 10,160,950 B2
APPLICATION NO. : 15/016934
DATED : December 25, 2018
INVENTOR(S) : Su-Chun Zhang et al.

It is certified that error appears in the above-identified patent and that said Letters Patent is hereby corrected as shown below:

In the Specification

Column 3, Line 36, "3" should be --3μ--.

Column 11, Line 53, "SHE" should be --SHH--.

Column 14, Line 38, "1-3" should be --1-3 μM,--.

Signed and Sealed this
Nineteenth Day of March, 2019

Andrei Iancu
*Director of the United States Patent and Trademark Office*

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: synthetic

<400> SEQUENCE: 1
caccacctcc catatgtcca gatt        24

<210> SEQ ID NO 2
<211> LENGTH: 23
<212> TYPE: DNA
<213> ORGANISM: Artificial Sequence
<220> FEATURE:
<223> OTHER INFORMATION: synthetic

<400> SEQUENCE: 2
gaatgtgagc accttccttc ttt        23

<210> SEQ ID NO 3
<211> LENGTH: 22
<212> TYPE: DNA
<213> ORGANISM: Artificial Sequence
<220> FEATURE:
<223> OTHER INFORMATION: synthetic

<400> SEQUENCE: 3
atgagctgtg agaagggtgt tg        22

<210> SEQ ID NO 4
<211> LENGTH: 22
<212> TYPE: DNA
<213> ORGANISM: Artificial Sequence
<220> FEATURE:
<223> OTHER INFORMATION: synthetic

<400> SEQUENCE: 4
ttgccacata cgcctcacat ac        22

```
<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
tttcactctt tgtggtcctc a                                             21

<210> SEQ ID NO 6
<211> LENGTH: 19
<212> TYPE: DNA
<213> ORGANISM: Artificial Sequence
<220> FEATURE:
<223> OTHER INFORMATION: synthetic

<400> SEQUENCE: 6
agaccctgga aatcgaagc                                                19

<210> SEQ ID NO 7
<211> LENGTH: 22
<212> TYPE: DNA
<213> ORGANISM: Artificial Sequence
<220> FEATURE:
<223> OTHER INFORMATION: synthetic

<400> SEQUENCE: 7
ctctctgctc ctcctgttcg ac                                            22

<210> SEQ ID NO 8
<211> LENGTH: 19
<212> TYPE: DNA
<213> ORGANISM: Artificial Sequence
<220> FEATURE:
<223> OTHER INFORMATION: synthetic

<400> SEQUENCE: 8
tgagcgatgt ggctcggct                                                19
```